United States Patent
Bourn et al.

(10) Patent No.: US 6,238,060 B1
(45) Date of Patent: May 29, 2001

(54) MACHINE-VISION RING-REFLECTOR ILLUMINATION SYSTEM AND METHOD

(75) Inventors: Charles T. Bourn, Minnetonka; Gary A. Lebens, Chaska, both of MN (US)

(73) Assignee: PPT Vision, Inc., Eden Prairie, MN (US)

( * ) Notice: Subject to any disclaimer, the term of this patent is extended or adjusted under 35 U.S.C. 154(b) by 0 days.

(21) Appl. No.: 09/499,250

(22) Filed: Feb. 7, 2000

Related U.S. Application Data

(62) Division of application No. 08/914,441, filed on Aug. 19, 1997, now Pat. No. 6,022,124.

(51) Int. Cl.⁷ .......................... F21Y 103/02; G03B 15/03
(52) U.S. Cl. ................... 362/216; 362/3; 362/33
(58) Field of Search ..................... 348/131, 132, 348/370, 371; 356/237; 359/387; 362/3, 11, 33, 216, 297, 346

(56) References Cited

U.S. PATENT DOCUMENTS

| | | | |
|---|---|---|---|
| 4,974,138 | * 11/1990 | Negishi | 362/297 |
| 5,179,474 | * 1/1993 | Bailey et al. | 359/387 |
| 5,457,492 | 10/1995 | Sasaki et al. | 348/126 |
| 5,745,176 | 4/1998 | Lebens | 348/370 |
| 5,825,495 | * 10/1998 | Huber | 356/237 |
| 5,828,449 | 10/1998 | King et al. | 356/237 |
| 6,084,631 | 7/2000 | Tonkin et al. | 348/212 |

OTHER PUBLICATIONS

"Communication from Client", *Vision Light Tech. BV*, 3 pages, (Apr. 4, 1997).
"Communication from Client", *Vision Light Tech. BV*, 1 page, (May 5, 1997).
"Copy of U.S. application Ser. No. 08/532,213, now issued U.S. Pat. No. 5,745,176, entitled "Machine–Vision Illumination System & Method"", 27 pgs (Oct. 12, 1995).
"Copy of U.S. application Ser. No. 08/825,774 entitled "High Speed Digital Video Serial Link"", 33 pgs., (Apr. 2, 1997), now U.S. Pat. No. 6,084,631.

* cited by examiner

*Primary Examiner*—Alan Cariaso
(74) *Attorney, Agent, or Firm*—Schwegman, Lundberg, Woessner & Kluth, P.A.

(57) ABSTRACT

An illumination method and apparatus for machine-vision systems, including a ring-light source (e.g., LEDs arranged in one or more circular rows), and a reflective-ring focusing element. The illumination source exhibits multidirectional ring-illumination properties which are useful for illumination of small components (which are being inspected or measured) without unwanted shadows. One embodiment provides a dark field illumination system. One embodiment of the present invention uses a strobed (or pulsed) power supply to drive the LEDs. Yet another embodiment of the present invention uses a xenon strobe ring-light source and a backplane slit in place of the row of LEDs. In one such xenon strobe embodiment, a color filter is also placed in series with the light path in order to obtain a monochromatic light. While xenon flashtube light sources tend to exhibit a five per cent (5%) flash-to-flash variation in intensity which makes accurate measurements of certain characteristics difficult, they are useful in certain cases where intense white, or especially ultraviolet, light is desired. Strobed LEDs provide very little flash-to-flash variation in intensity. The compact ring-light generator has little, if any, shadowing. The present invention also provides an inexpensive apparatus and method for changing the light-source-to-optical-axis angle.

22 Claims, 22 Drawing Sheets

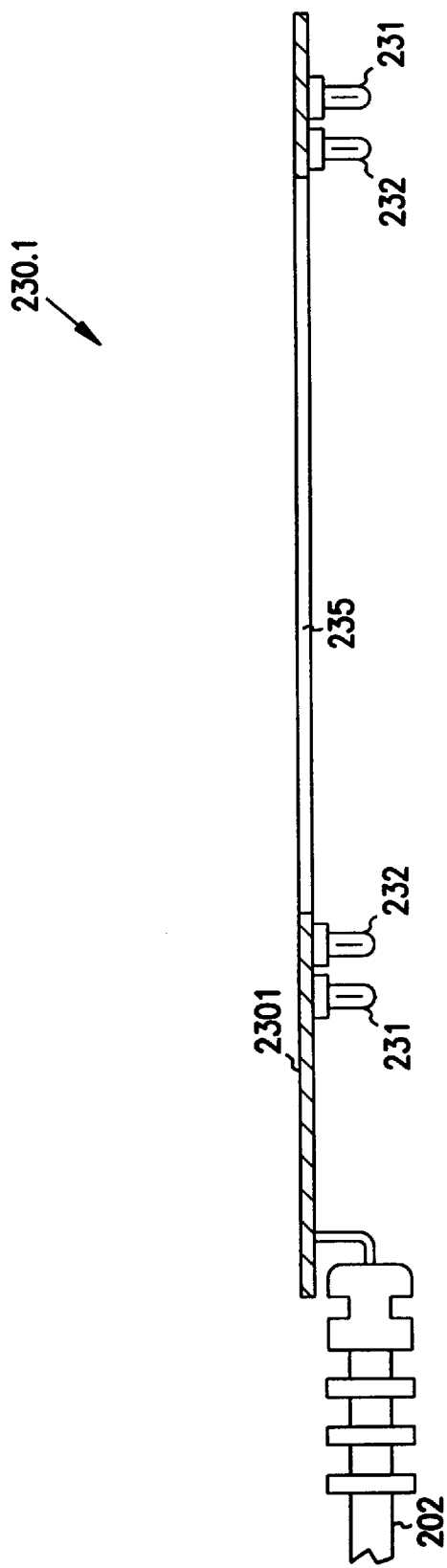

MACHINE-VISION RING-REFLECTOR ILLUMINATION SYSTEM AND METHOD

This application is a divisional of U.S. patent application Ser. No. 08/914,441, filed Aug. 19, 1997, now U.S. Pat. No. 6,022,124 which application is incorporated by reference.

TECHNICAL FIELD OF THE INVENTION

The present invention pertains generally to illumination optics, and more particularly systems and methods for illumination of objects in machine-vision systems.

BACKGROUND OF THE INVENTION

During the manufacture of certain products, such as electrical components, it is necessary to be able to provide high-intensity illumination so that components can be thoroughly inspected with a machine-vision system. Often, the light source needed includes one or more light sources, for example a ring-shaped flashtube or a number of light-emitting diodes arranged along a circle or a remote light source that drives light into a number of optical fibers arranged along a circle, surrounding the lens of a video camera such that the object being imaged by the video camera is illuminated with light angled in towards the optical axis of the camera from the light source surrounding the lens. It is desirable that the light source or sources are arranged such that no light shines directly from the light sources into the lens.

Typically, a xenon flashtube or laser-based single-point source or other high-intensity light source is used for providing light into fiber-optic-based ring source. Such systems, however, are costly, very large and bulky, and can interfere with the placement of other components in the machine-vision system. This is particularly troublesome when the components being measured or inspected are extremely small. Xenon flashtube light sources also tend to exhibit up to about a five per cent (5%) flash-to-flash variation in intensity which makes accurate measurements of certain characteristics difficult. Single-point source systems are also generally limited to emitting light radially from only one single point, which is of limited value when shadows are problematic, such as, when inspecting a grid of electrical connectors. Specifically, light from only one or just a few point sources only illuminates the first over-sized or over-height electrical connector and, due to shadows from the first object encountered, does not provide proper illumination which would determine if other objects behind this particular first object are missing, of the incorrect size or height, or perhaps in the wrong position.

Conventional illumination systems produce a light which can be too bright in certain areas and too dim in other areas. Often, the end-result is "bloom", especially when viewing white, lightly colored, or very reflective objects which are near other objects which need to be viewed by a machine-vision camera. In order to get enough light on the other objects which need to be viewed, the aperture on the camera cannot be "stopped down" in order to prevent overexposure of the bright objects. Specifically, the area is illuminated to such an extent that the entire image appears to be the same bright saturated white color (or, if a monochromatic light source is used, saturated at whatever color is used) as viewed by the machine-vision camera and system. Such extreme brightness also poses a danger of blinding, at least temporarily, human workers nearby.

Quite often, illumination sources either leave certain portions of the scene in shadows, or provide too much light in certain areas, while leaving other areas with too little light. In other cases, the illumination source is too bulky and gets in the way of other components of the machine-vision system, associated robots, manipulators, and/or human workers.

The optimal light-source-to-optical-axis angle can vary depending on the object being inspected. One shortcoming of conventional ring light sources is the cost and difficulty in changing the angle between the light sources relative to the optical axis, and in changing the spread and/or focus of the light from ring-light source.

Thus, what is needed is an ring-light illumination system and method which is compact, provides control over both the angle between the light source and the optical axis of the camera, as well as the spread and/or focus of the light from ring light source, so that even extremely small parts can be quickly and adequately inspected and accurately viewed or measured with a machine-vision system. Another need is to provide a compact illumination source, preferably monochromatic, which can be focused to provide uniform multi-directional light onto objects from all sides while avoiding light going directly from the light sources to the lens of the camera. Another need is to provide a compact monochromatic LED (light-emitting diode) illumination source, which can be changeably focused to provide uniform multi-directional light onto objects. Another need is to have such an LED illumination source be pulsed with a relatively high-power, low duty-cycle power source.

SUMMARY OF THE INVENTION

The present invention takes advantage of the efficiency of high-brightness red, infra-red, blue, white, or other color LEDs arranged in one or more circular rows, and the properties inherent to a reflective focusing element such as a turned angled reflective ring to produce an illumination source for machine-vision systems. The illumination source exhibits multi-directional ring-illumination properties which are useful for illumination of small components (which are being inspected or measured) without unwanted shadows. One embodiment provides a darkfield illumination system. One embodiment of the present invention uses a strobed (or pulsed) power supply to drive the LEDs. Yet another embodiment of the present invention uses a xenon strobe ring-light source and a backplane slit in place of the row of LEDs. In one such xenon strobe embodiment, a color filter is also placed in series with the light path in order to obtain a monochromatic light. While xenon flashtube light sources tend to exhibit a five per cent (5%) flash-to-flash variation in intensity which makes accurate measurements of certain characteristics difficult, they are useful in certain cases where intense white, or especially ultraviolet, light is desired.

The present invention provides a compact ring-light generator which has little, if any, shadowing. The present invention also provides an inexpensive method for changing the light-source-to-optical-axis angle. The present invention also provides an inexpensive method for changing the spread and/or focus of the light from ring light source.

The present invention provides a method and apparatus which provide an illumination source for illuminating an object in a machine-vision system having a machine-vision camera, the camera having an optical axis. One embodiment of the illumination source includes a ring-light source emitting light from a plurality of points, the points being along one or more circles, a focusing element, the focusing element including an angled ring reflector to direct rays from the ring light source at an angle generally towards the optical axis. One embodiment provides a replaceable ring reflector for changing the light-source-to-optical-axis and/or changing the spread and/or focus of the light from ring light source. One embodiment provides light from multiple directions in order to reduce shadowing. One embodiment provides light to illuminate the inside of, for example, an aluminum beverage can before it is filled and sealed.

One embodiment uses a ring-reflector focusing element which includes a first conical section reflective surface at a first conical angle to the optical axis. Another embodiment further includes a second conical section reflective surface at a second conical angle to the optical axis.

One embodiment includes an illumination source for illuminating an object in a machine-vision system, the system having an optical axis. The illumination source includes a ring light source and a ring reflector. The ring light source emits light from a plurality of points or from a line, the points or line being substantially in a plane that intersects the optical axis, each of the points or the line disposed at least a first distance from the optical axis and less than a second distance from the optical axis. The ring reflector has an exit opening though which the optical axis passes, the emitted light from the ring light source being generally directed centered on lines that intersect a reflecting surface of the ring reflector, the ring reflector reflecting the emitted light from the light source though the exit opening inwards and generally towards the optical axis or an area around the optical axis.

In one such embodiment, the ring light source includes a plurality of light-emitting diodes (LEDs) arranged substantially along a circle disposed perpendicular to and centered on the optical axis. In another such embodiment, each LED has an focal centerline emission axis along which emission is centered, and each LED's emission axis is parallel to the optical axis. In yet another such embodiment, each LED has an focal centerline emission axis along which emission is centered, and each LED's emission axis is perpendicular to the optical axis.

In one embodiment, the light emitted from the LEDs is two or more selected from the following: infra-red, red, amber, yellow, green, blue, violet, ultraviolet, or white in color. In another such embodiment, the light emitted from the LEDs is primarily within an angle of about 5° from a focal centerline of each individual LED.

One embodiment further includes a focusing element that includes a cylindrical ring lens having at least one convex face.

In one embodiment, the ring light source includes a ring-shaped flashtube located substantially along a circle disposed perpendicular to and centered on the optical axis, and further includes an enclosure having a slit located between the ring-shaped flashtube and the ring reflector, wherein the slit allows light from the flashtube to fall on a reflecting surface of the ring reflector.

In one embodiment, the ring reflector has a surface that enhances its reflectivity at one or more selected wavelengths of the ring light source.

In one embodiment, the ring reflector and ring light source are configured to produce a darkfield illumination.

Another aspect of the present invention is a method for illuminating an object located along an optical axis. The method includes the steps of (a) emitting light from a plurality of points or from a line, the points or line being substantially in a plane that intersects the optical axis, each of the points or the line disposed at least a first distance from the optical axis and less than a second distance from the optical axis; and (b) reflecting the emitted light from the light source inwards and generally towards the object at the optical axis or in an area around the optical axis.

In one such embodiment, the object is an electrical connector, and the method further includes the step of acquiring a machine-vision image of the electrical connector. One application for such a method is inspecting ball-grid arrays.

Another aspect of the present invention provides a machine-vision illumination system. The system includes an imaging device, an image processor coupled to the imaging device, and an illumination source coupled to the image processor. The illumination source includes a ring light source and a ring reflector. Other aspects of such a system are described above.

Another aspect of the present invention provides a ring reflector for use in reflecting light from a ring light source The ring reflector includes a substantially circular exit opening though which the optical axis passes and a reflective surface surrounding the exit opening. The reflective surface extends from approximately a first circle having a first radius, to approximately a second circle and having a second radius, the second radius being larger than the first radius, the first radius being larger than the difference between the second radius and the first radius.

In one such embodiment, the reflective surface includes a conical section. In another such embodiment, the reflective surface includes a plurality of adjoining conical sections. In yet another such embodiment, the reflective surface includes a circularly-rotated parabolic section. In still another such embodiment, the reflective surface includes a plurality of reflective facets. In one such embodiment, for a plurality of the facets, a line normal to the facet surface passes through the optical axis. Another aspect of the present invention provides a reflective surface that is configurable to change the angle at which it reflects light.

These and other features, aspects, and advantages of the present invention will become better understood with regard to the following description, appended claims and accompanying drawings.

BRIEF DESCRIPTION OF THE DRAWINGS

FIG. 2D is a cut-away side view of another ring-light source 230 using LEDs according to one embodiment of the present invention.

DETAILED DESCRIPTION OF THE INVENTION

In the following detailed description of the preferred embodiments, reference is made to the accompanying drawings which form a part hereof, and in which are shown, by way of illustration, specific embodiments in which the invention may be practiced. It is to be understood that other embodiments may be utilized and structural changes may be made without departing from the scope of the present invention.

The present invention provides a method and system for generating rays of light with suitable brightness and evenness from a source surrounding, for example, the lens of a machine-vision camera The rays are directed generally towards the optical axis of the camera. One embodiment provides a diffuse source circumferentially such that even extremely small objects can be adequately inspected and accurately measured by a machine-vision system 100.

The unique ability of the method and apparatus of the LED illumination system of the present invention to provide an inexpensive and changeable light source within these constraints distinguishes this system from other illumination systems purporting to provide suitable high-intensity illumination for machine-vision inspecting or measuring purposes.

An illumination system is described in MACHINE-VISION ILLUMINATION SYSTEM AND METHOD, U.S. patent application Ser. No. 08/532,213, filed Oct. 12, 1995, by Gary A. Lebens and assigned to PPT Vision, Inc., the assignee of the present invention, and which is hereby incorporated by reference.

A serial machine-vision interconnection system is described in HIGH-SPEED DIGITAL VIDEO SERIAL LINK, U.S. patent application Ser. No. 08/825,774, filed Apr. 2, 1997, which is a file-wrapper continuation of Ser. No. 08/410,119, filed Mar. 24, 1995 by Joseph C. Christianson and Larry G. Paulson and assigned to PPT Vision, Inc., the assignee of the present invention, and which is hereby incorporated by reference.

Figure 1A:
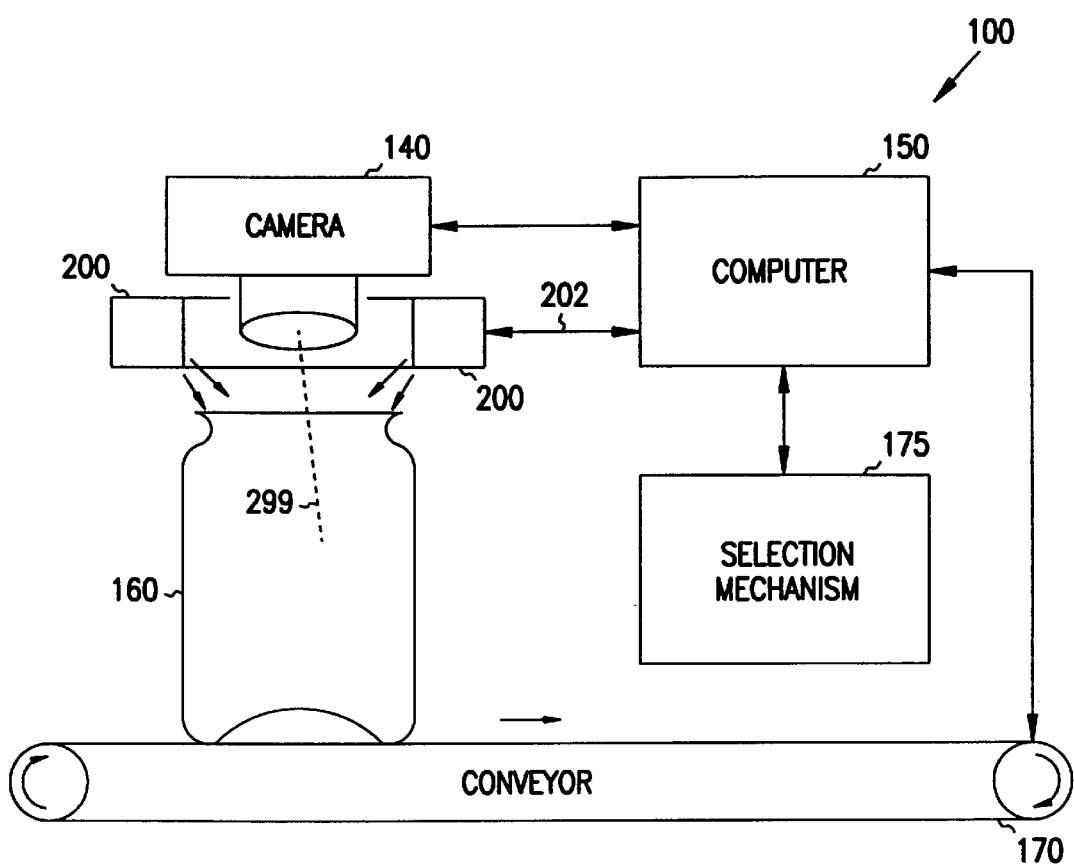
FIG. 1A is a side-view schematic diagram of one embodiment of machine-vision illumination system 100.

FIG. 1A is a side-view schematic diagram of an embodiment of machine-vision illumination system 100 according to the present invention. In FIG. 1, an object 160 (for example, a beverage can or other food or drink container, or an electronics assembly or other manufactured item) is illuminated for inspection by a machine-vision camera (or other imaging device) 140 which is coupled to computer/image processor 150. In this embodiment, camera 140 is disposed to view object 160 through an opening in ring-reflector illumination source 200 which directs light downward and inward. In the exemplary system shown, it is desired to illuminate the top edge, inside walls and inside bottom surface of object 160 for viewing by camera 140 with even, high intensity, short-duration illumination of a fixed intensity. In one embodiment camera 140 is a video camera, such as a Panasonic model GPMF702, having a telecentric lens, such as an Invaritar-brand lens made by Melles-Griot. In one such embodiment, the telecentric lens, which has uniform magnification across the field of view, of camera 140 is made larger in diameter than the diameter of object 160 being viewed (e.g., one embodiment uses a 6-inch diameter lens for 3-inch diameter objects) in order to reduce lens distortion, such as pin-cushioning and barrel distortion. Camera 140 is coupled to image processor 150 with suitable cables, for example, a digital-serial link such as described in patent application Ser. No. 08/825,774 cited above, or other suitable electrical or fiber-optical signal cables. In one embodiment, camera 140 is positioned above and facing objects 160 moving by action of conveyor mechanism 170 across the camera field of view, so that camera 140 can obtain and send a captured image of object 160 to image-processing computer 150. In one embodiment, computer 150 analyzes the captured image and activates selection mechanism 175 to accept or reject each successive object (e.g., diverting rejected items into a reject bin) based on predetermined criteria, all using methods and apparatus well known to those skilled in the art of machine vision.

Camera 140 is implemented as any one of a number of device technologies including vidicon, CCD (charge-coupled device) line- or array-imaging devices, metal-oxide semiconductor (MOS) video cameras, and so forth. In one embodiment, camera 140 is a solid-state MOS camera having a peak wavelength sensitivity of about 550 nanometers (nm), and range of approximately 500 to 600 nm at about 97% of peak. In one embodiment, the aperture on the lens of camera 140 is suitably small in order that a relatively large depth-of-field is obtained. The type and size of lens is chosen to match the field-of-view to the size/depth of object 160.

Figure 1B:
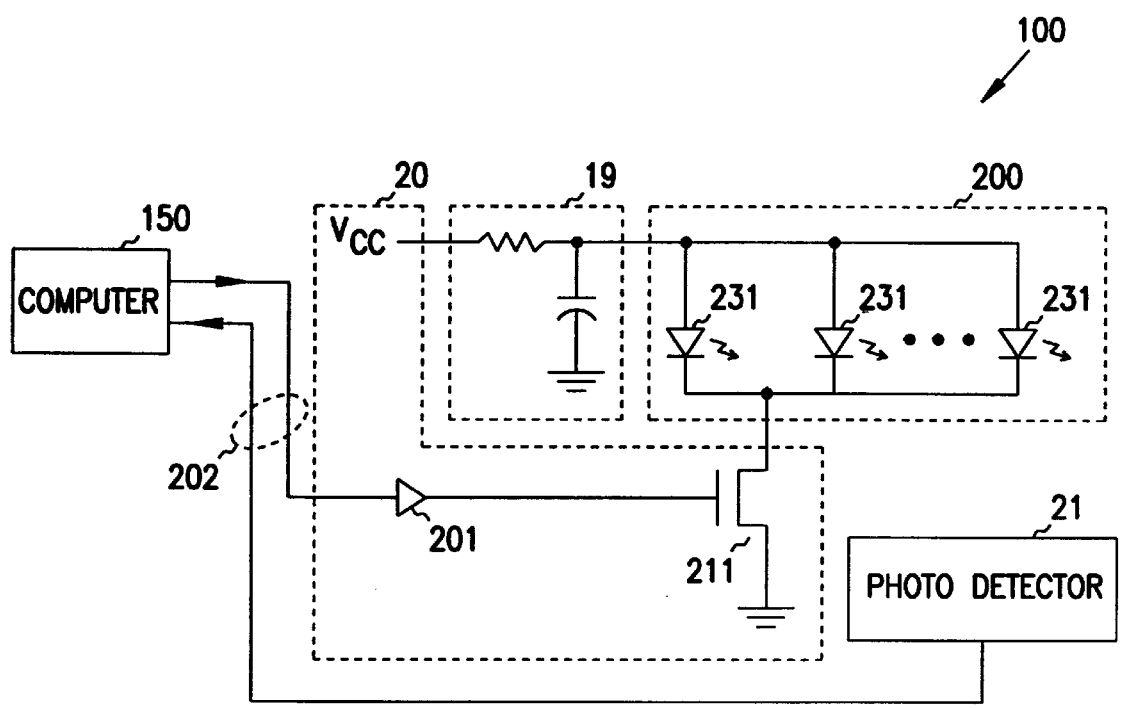
FIG. 1B is a circuit schematic diagram of a portion of one embodiment of machine-vision illumination system 100.

In one embodiment, shown in FIG. 1B (FIG. 1B is a circuit schematic diagram of a portion of one embodiment of machine-vision illumination system 100), each ring-reflector illumination source 200 is connected to a capacitor box 19, which is connected to a power supply 20, which is connected to image processor 150. The charge on capacitor box 19 is discharged through LEDs 231 in ring-reflector illumination source 200 when computer 150 drives a pulse on signal cable 202 to amplifier 201 which in turn drives power MOSFET (metal-oxide-semiconductor field-effect transistor) 211 to substantially short to ground. In one embodiment, a short-duration pulse (approximately 10 microseconds to 100 microseconds long) to provide a short, intense pulse of light. Further details of power supply 20 and capacitor box 19 are found on Ser. No. 08/532,213 cited above. In one such embodiment, a photodetector 21 is used to detect the light output and provides feedback to computer 150 which is used to control the duration or frequency of the light pulses.

In the embodiment shown in FIG. 1, ring-reflector illumination source 200 is enclosed to light except for the lens opening 245 through back plate 240 and opening 225 in ring reflector 220.

Figure 2A:
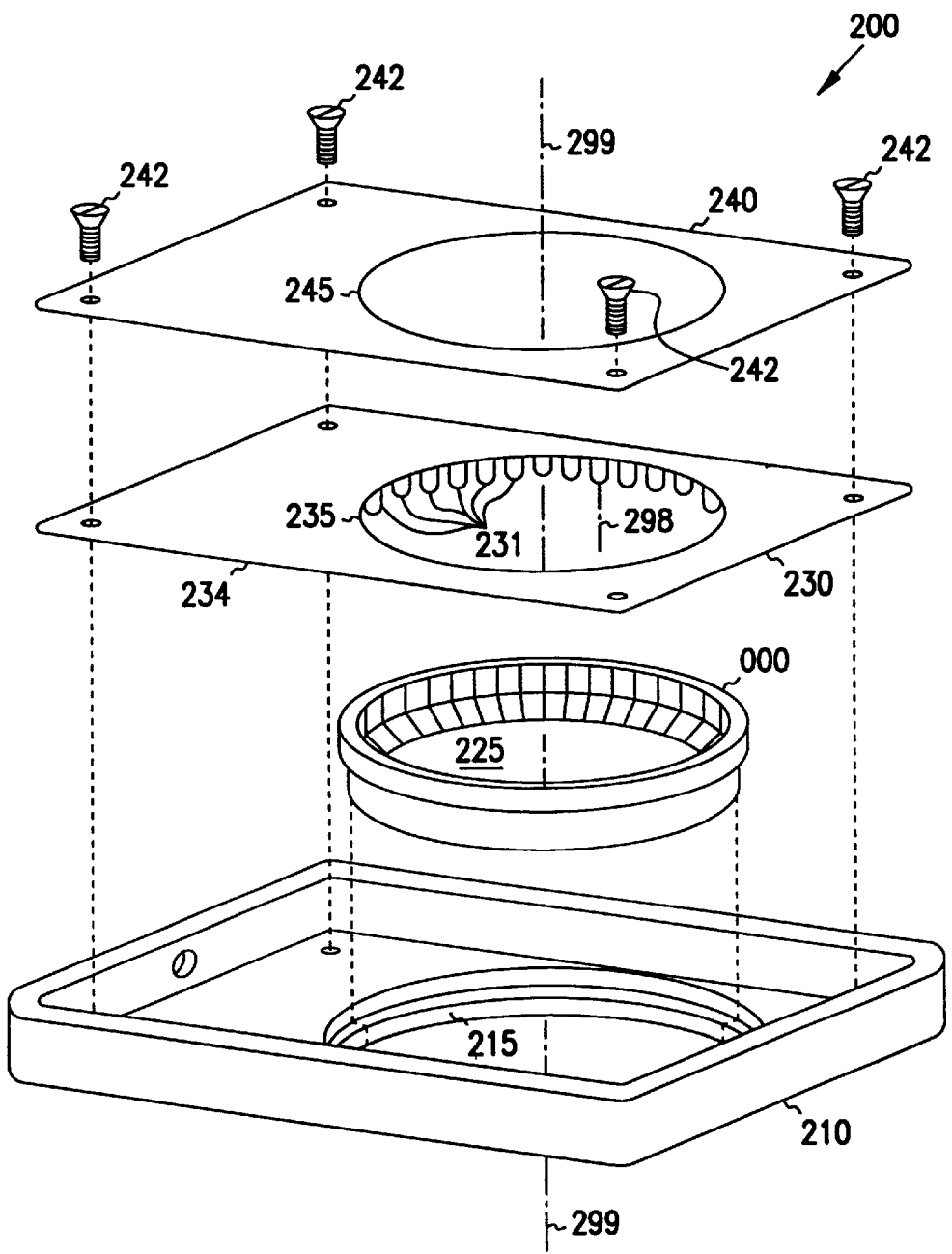
FIG. 2A is an exploded isometric view of ring-reflector illumination source 200 according to one embodiment of the present invention.

FIG. 2A is an exploded isometric view of ring-reflector illumination source 200 according to one embodiment of the present invention. Ring-reflector illumination source 200 includes bottom enclosure 210, replaceable/changeable ring reflector 220, ring illumination source 230 (in this embodiment, this is an LED light source 230 having a single row of LEDs arranged in a circle that is centered on optical axis 299 of camera 140, the focal centerlines 298 of each LED is directed along a line parallel to optical axis 299), and top cover 240 that is attached to bottom enclosure 210, for example by four screws 242. In the embodiment shown, bottom enclosure 210 has an opening 215 having a lip or collar into which reflector ring 220 fits.

It is contemplated that a user will have more than one reflector ring 220, each having a different reflective angle or reflective configuration/focus, so that the ring reflector 220 in ring reflector illumination source 200 may be changed according to the needs of the object being inspected, the particular camera or lens being used, etc., without replacing other parts in ring-reflector illumination source 200. Alternatively, a configurable ring reflector 2205 can be used in place of multiple replaceable/changeable ring reflectors 220, thus allowing the user to change the reflective angle or reflective configuration/focus by changing the configuration of reflector 2205 (explained further below). It is further contemplated that a user may have more than one ring-light source 230, each having a different configuration of LEDs, dispersion angle, color or wavelength configuration, intensity or pulse response, so that the ring-light source 230 in ring-reflector illumination source 200 may be changed according to the needs of the object being inspected, the camera being used, etc., without replacing other parts in ring-reflector illumination source 200. FIG. 2A shows one configuration that makes possible the exchange of ring reflector 220 and/or ring-light source 230, however other configurations are contemplated that make changing of the ring reflector 220 and/or ring-light source 230 easier and faster, such as by threading with matching complementary threads the outer circumference of ring-light source 230 and the inner circumference of opening 215, such that ring reflector 220 can be exchanged without otherwise disassembling ring-reflector illumination source 200.

Figure 2B:
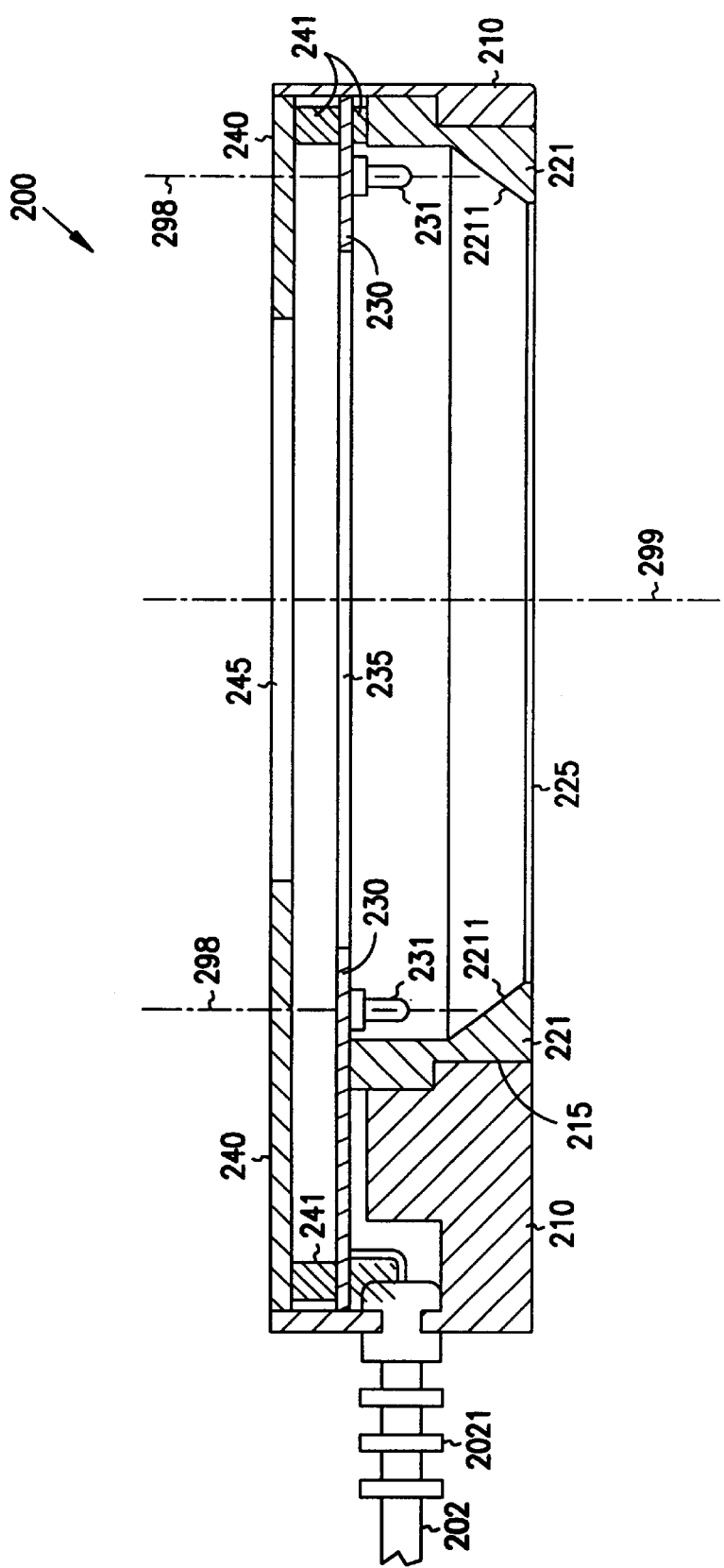
FIG. 2B is a cut-away side view of ring-reflector illumination source 200 according to one embodiment of the present invention.

FIG. 2B is a cut-away side view of ring-reflector illumination source 200 according to one embodiment of the present invention. In the embodiment shown, ring-reflector illumination source 200 includes bottom enclosure 210, replaceable/changeable ring reflector 220 (designed to fit into a complementary opening 215 in bottom enclosure 210), ring illumination source 230 (in this embodiment, this is an LED light source 230 having a single row of LEDs 231 closely spaced in a circle that is centered on optical axis 299 of camera 140, the focal centerlines 298 of each LED directed along a line parallel to optical axis 299), and top cover 240 that is attached to bottom enclosure 210, for example by four screws 242 that pass through spacers 241 used to maintain the desired spacing and placement of the LED light source 230 within ring-reflector illumination source 200. In one embodiment (see FIG. 2C), LED light source 230 includes a printed circuit board 2300 onto which are soldered (or otherwise mechanically and electrically connected) a plurality of individual LEDs 231 (e.g., in one embodiment, high-brightness red LEDs 1200 millicandles (mcd) at a peak wavelength of approximately 621 nm., for example, HLMA-KH00-type T1-sized lights having a half-angle of approximately 22.5° available from Hewlett-Packard; In another embodiment, a Toshiba part number TLRH160 emitting red light (644 nm at 1800 typical mcd) with a 5-degree half angle is used), spaced as closely as possible in a single row, the row centered on a circle that is perpendicular to and has a center on the optical axis 299. (In other embodiments, other LEDs having different colors/wavelengths, half-angles, intensity, or power capabilities are used. In one such embodiment, LED light source 230 is configures to be replaced/changed in order to let the user choose a suitable combination of colors/wavelengths, half-angles, intensity, or power capabilities for a particular application.)

In the following discussion, ring reflector 220 refers generally to any ring reflector (e.g., ring reflector 221 of FIG. 3A, ring reflector 222 of FIG. 3B, ring reflector 223 of FIG. 3C, or ring reflector 224 of FIG. 3D, or other similar ring reflector). Similarly, ring light source 230 refers generally to any ring light source (e.g., ring light source 230.0 of FIG. 2C, ring light source 230.1 of FIG. 2D, ring light source 230.2 of FIG. 2E, ring light source 236 of FIG. 2F, or other similar ring light source).

In the embodiments shown in FIGS. 2A–2F, printed circuit board (PCB) 2300 has a circular opening 235 also having a center on the optical axis 299. Signal wire 202 passes through insulating strain relief 2021 which is mounted to bottom enclosure 210. Signal wire 202 is soldered to PCB 2300, which then distributes the electrical power from signal wire 202 to each of the LEDs 231.

Figure 2C:
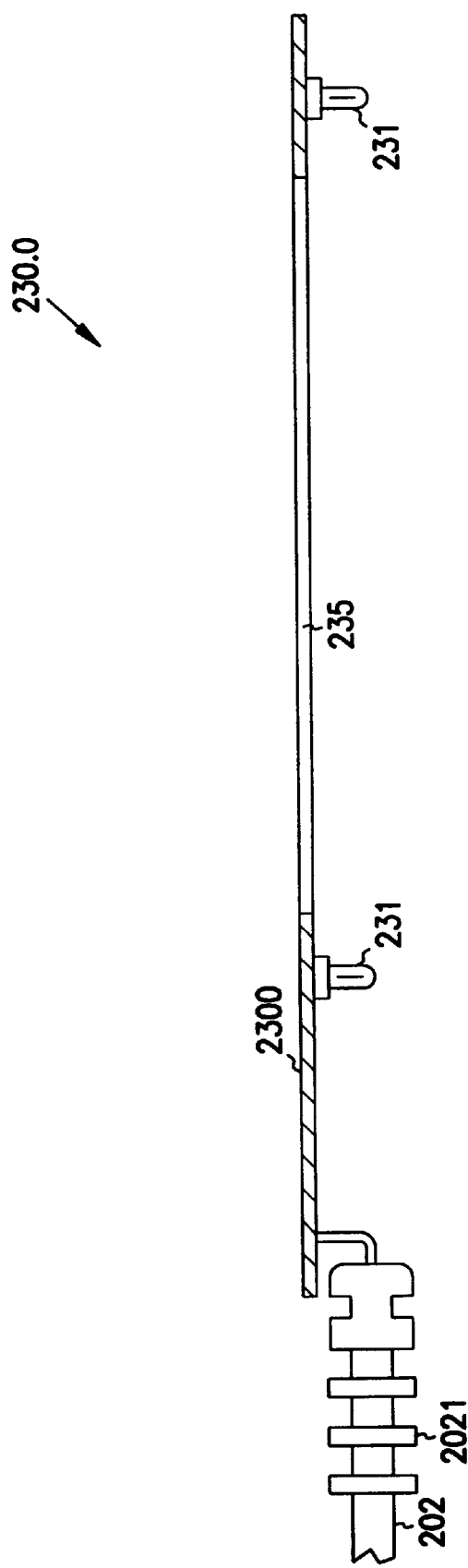
FIG. 2C is a cut-away side view of one ring-light source 230 using LEDs according to one embodiment of the present invention.

FIG. 2C is a cut-away side view of one ring-light source 230 using a single circular row of LEDs 231 according to one embodiment of the present invention. In one embodiment, all LEDs 231 are of the same color and type In another such embodiment, a mix of LED colors are used in order to get a polychromatic light. In yet another such embodiment, white phosphor/LED devices, such as a blue LED having a broad-spectrum phosphor that absorbs the blue light and re-emits a broad-spectrum centered at yellow to achieve a compact, very-long-life, efficient white light source (e.g., white LEDs such as manufactured by Nichia Chemical Industries, Ltd. of Japan; for example Part No. NLPB 510; see internet address http://www1a.meshnet.or.jp/nichia/wled-e.htm) are used in order to get a polychromatic, white-appearing light. In one embodiment, a pulsed electrical drive current is used (described in further detail below) in order to increase light efficiency (particularly during the time that the camera 140 is and/or to strobe the light pulse thereby reducing any blurring due to motion of the object being observed. In another embodiment, a direct-current (DC) electrical drive is used.

Figure 2E:
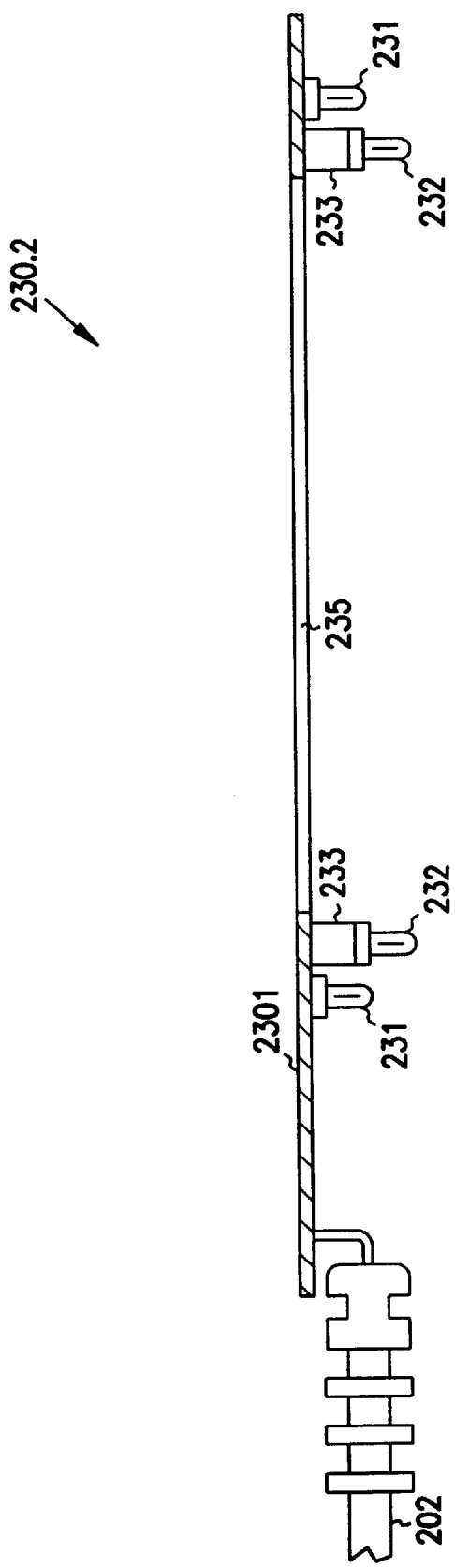
FIG. 2E is a cut-away side view of yet another ring-light source 230 using LEDs according to one embodiment of the present invention.

In the embodiments shown in FIGS. 2C–2E, each individual LED 231 and 232 has a built in focussing arrangement, typically including a cone-shaped reflector holding an LED chip, and a convex plastic lens package, that together direct and "focus" the light emitted from the LED chip in a direction centered about a focal centerlines 298 along an axis of the package. Such LED packages can be purchased at a number of dispersion angles (generally specified as the "half-angle" for the LED package), and at a variety of intensity capabilities (generally specified as millicandles (mcd) or milliwatts (mw) of light output). Conventionally, this arrangement has required that the axis of each LED package be pointed in the direction that light is wanted, i.e., at one or another angle pointed obliquely towards the optical axis of camera 140. It has been expensive to fabricate such a ring of LEDs, each pointed obliquely towards the optical axis of camera 140. Further, it is cumbersome and expensive to change the angle at which the LEDs point towards the optical axis (i.e., to move the angle of all of the LEDs, or to replace the ring with another having the desired angle.

The present invention provides an inexpensive and elegant solution to these problems. By providing an LED ring-light source having all the LEDs with the axes of their packages (i.e., the LED's individual focal centerlines 298) aligned parallel to the optical axis 299 (i.e., perpendicular to PCB 238), the cost of manufacture is minimized. In order to direct the light obliquely towards the optical axis 299, one or more inexpensive and easily changeable reflective rings 220 are provided. In order to change the intensity of light provided, a variable pulse-width and/or variable pulse-frequency LED power supply is provided.

FIG. 2D is a cut-away side view of another ring-light source 230 using a circular double row of LEDs 231 and 232 according to another embodiment of the present invention. In this embodiment, PCB 2301 is configured to mechanically and electrically connect to two rows of LEDs (outer circular row 231 and inner circular row 232). In one such embodiment, a two-angle reflector (e.g., 222 or 224 of FIG. 3B or FIG. 3D) is used, and the outer row 231 of LEDs is reflected at a shallow angle (e.g., by a face 2222 that is at an angle of approximately 53 degrees from the plane of exit opening 225) in order to achieve a deep area of illumination (i.e., further from exit opening 225), and the inner row 232 of LEDs is reflected at a less-shallow angle (e.g., by a face 2221 that is at an angle of approximately 47 degrees from the plane of exit opening 225) in order to achieve a shallower area of illumination (i.e., closer to exit opening 225). In one embodiment, both rows of LEDs (231 and 232) are simultaneously illuminated, in order to simultaneously get both deep and shallow illumination. In another embodiment, each row is flashed at different times, in order to get either deep or shallow illumination.

FIG. 2E is a cut-away side view of yet another ring-light source 230 using a circular double row of LEDs 231 and 232, wherein row of LEDs 232 is mounted at a small distance from PCB 2301, for example, by inserting spacers 233 between each LED and the PCB 2301, according to another embodiment of the present invention. In this embodiment, PCB 2301 is configured the same as for FIG. 2D, however, spacers 233 or other means, are used to drop the position of LEDs 232 relative to the PCB 2301, thus moving the plane of the circle for those LEDs closer to ring reflector 220 (e.g., ring reflector 222, 223 or 224).

Figure 2F:
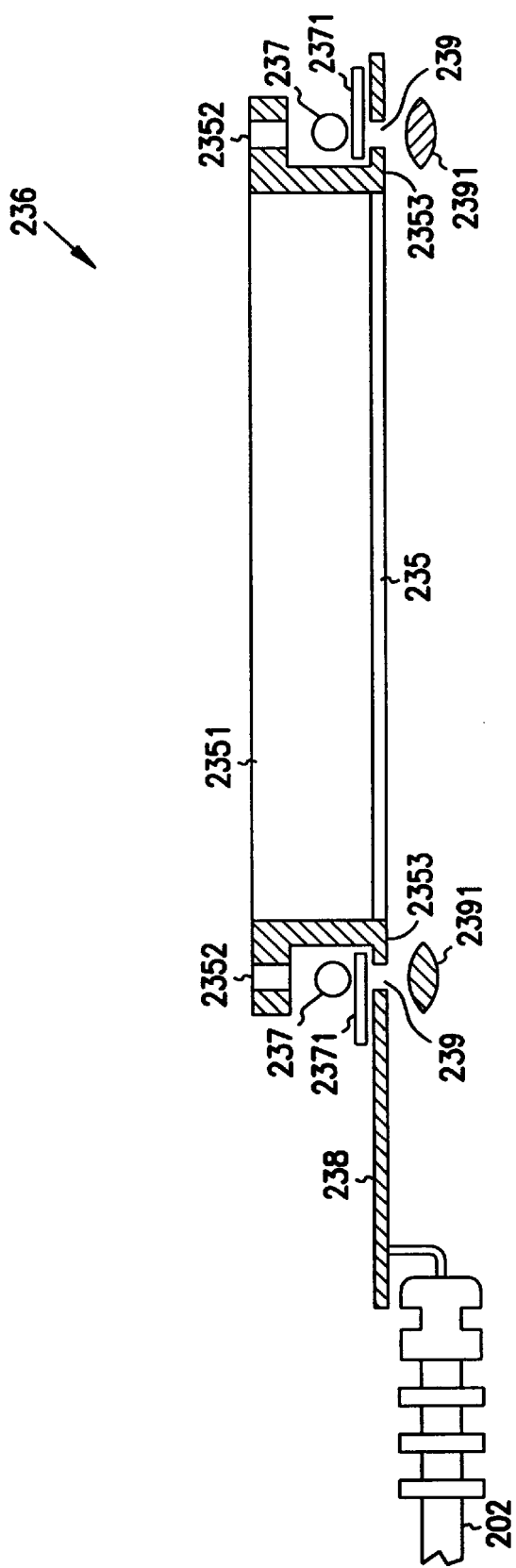
FIG. 2F is a cut-away side view of ring-light source 236 using a xenon flashtube according to one embodiment of the present invention.

FIG. 2F is a cut-away side view of ring-light source 236 using a xenon flashtube according to one embodiment of the present invention. In one embodiment, a xenon strobe light source 237, e.g., any suitable circular short-arc flashlamp bulb, and a diaphragm 238 having backplane slit 239, are used in place of the row of LEDs. In one such embodiment, raised collar 2351 is fabricated to be bolted to top cover 240 through screw holes 2352, then inner slit ring 2353 (having opening 235) is fastened to the lower edge of collar 2351, in order that only light passing through slit 239 is used (i.e., reflected and directed by ring reflector 220). The gap between the outer circumference of slit ring 2353 and the inner edge of the hole 2381 in diaphragm 238 defines a continuous (e.g., circular) slit 239 having no breaks. In another embodiment (see FIG. 2G which shows four struts holding the inner ring to the diaphragm 238), such breaks are due to, for example, support struts that are needed to hold inner slit ring 2382 to diaphragm 238. In one such xenon strobe embodiment, an optional color filter 2371 is also placed in series with the light path in order to obtain a monochromatic light, which can be more sharply focused by the lens of camera 140 than white light.

In one such xenon strobe embodiment, an optional circular cylindrical ring lens 2391 (i.e., equivalent or similar to the cross-section of a convex-convex cylindrical lens as shown, that is rotated in a circle centered on optical axis 299; another embodiment uses a plano-convex) is also placed in series with the light path in order to focus light from the circular xenon source (i.e., focusing the emitted light to a circular line). In another embodiment, such a cylindrical ring lens 2391 is placed in series with light emitted from a ring-LED source such as ring light source 230.0 of FIG. 2C.

Figure 2G:
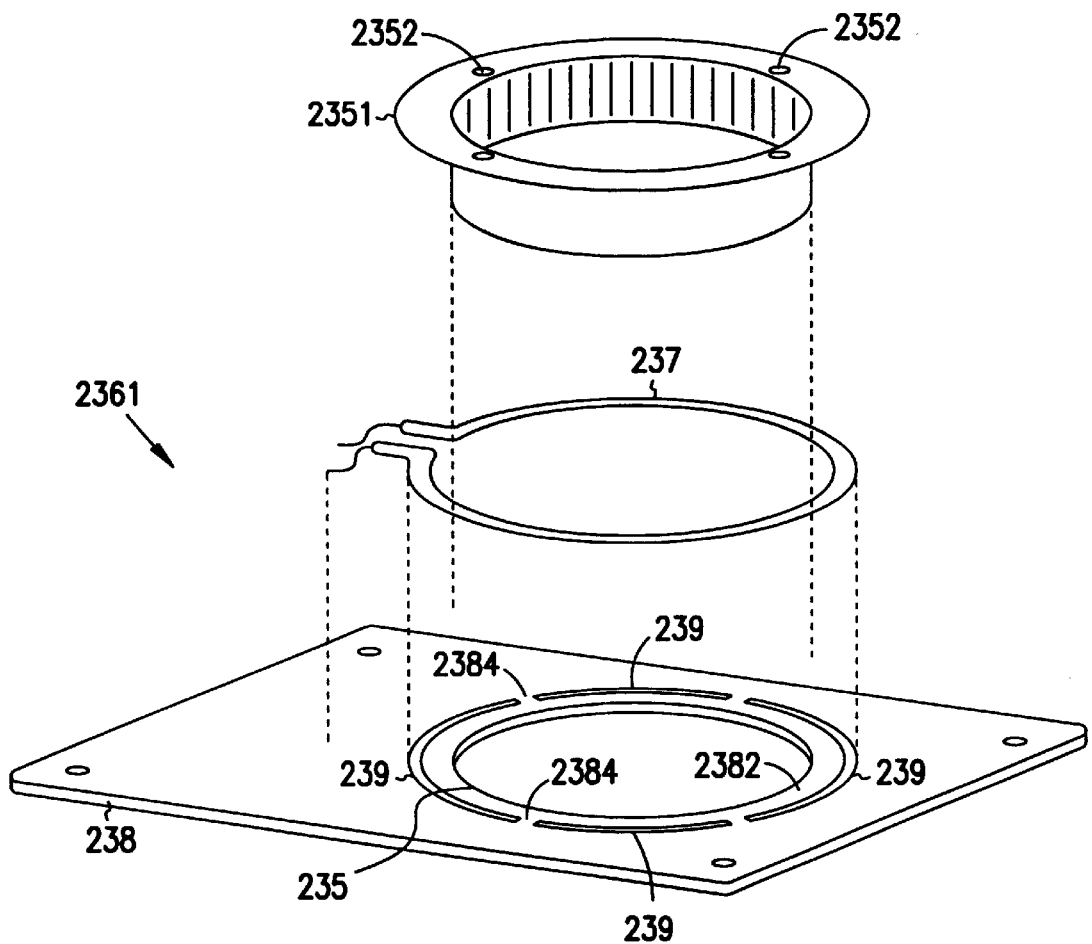
FIG. 2G is an exploded isometric view of a flash-tube light source 2361 according to one embodiment of the present invention.
Figure 2H:
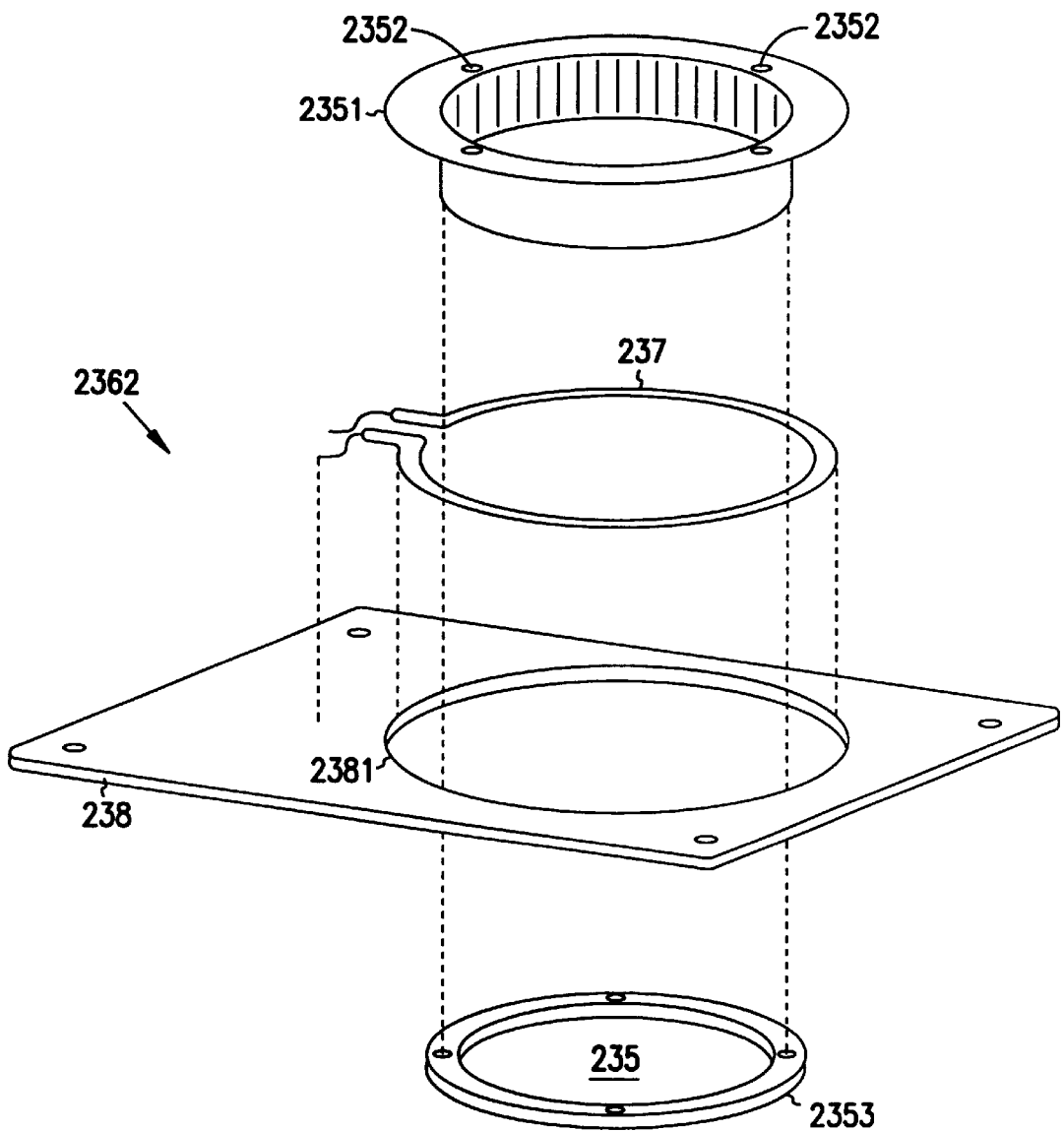
FIG. 2H is an exploded isometric view of a flash-tube light source 2362 according to one embodiment of the present invention.

Ring-light source 236 refers generally to a flashtube-slit assembly such as flash-tube light source 2361 of FIG. 2G or flash-tube light source 2362 of FIG. 2H. In some embodiments, flashtube 237 is replaced by a similarly shaped enclosed incandescent filament circular tube, or a fluorescent circular tube, or linear LED chips arranged in a polyhedron, or other continuous circular light source.

FIG. 2G is an exploded isometric view of a flash-tube light source 2361 according to one embodiment of the present invention. Struts 2384 hold inner slit ring 2382 to diaphragm 238. Raised collar 2351 is fabricated to be bolted to top cover 240 through screw holes 2352, and for its lower edge to be light-tight against inner slit ring 2382 when assembled in ring-reflector illumination source 200.

FIG. 2H is an exploded isometric view of a flash-tube light source 2362 according to another embodiment of the present invention. In this embodiment, as described above, raised collar 2351 is fabricated to be bolted to top cover 240 through screw holes 2352, then inner slit ring 2353 (having opening 235) is fastened to the lower edge of collar 2351, in order that only light passing through slit 239 is used (i.e., reflected and directed by ring reflector 220). The gap between the outer circumference of slit ring 2353 and the inner edge of the hole 2381 in diaphragm 238 defines a continuous (e.g., circular) slit 239 having no breaks.

Figure 2I:
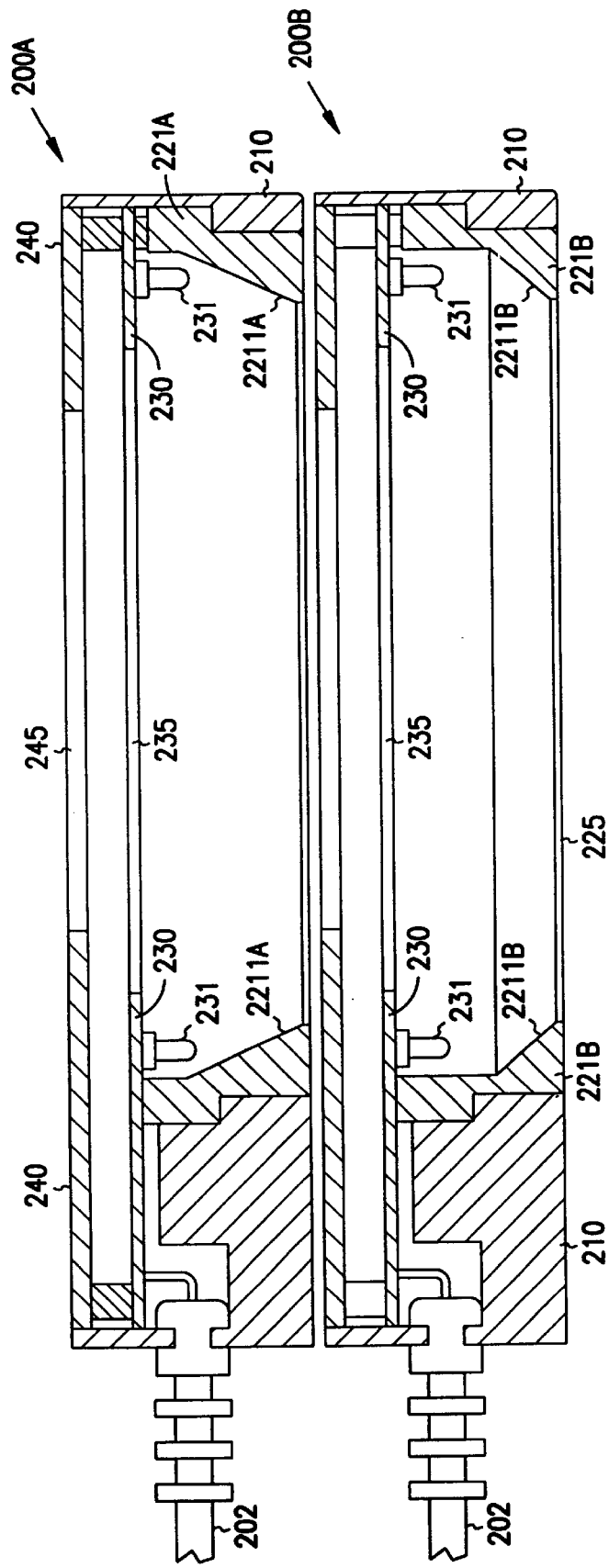
FIG. 2I is a cut-away side view of two stacked ring-reflector illumination sources 200A and 200B according to one embodiment of the present invention.

FIG. 2I is a cut-away side view of two stacked ring-reflector illumination sources 200A and 200B according to one embodiment of the present invention. In this embodiment, ring-reflector illumination source 200A is configured to have the light from its LEDs 231 reflected at a shallow angle (e.g., by a face 2211A that is at an angle of approximately 53 degrees from the plane of exit opening 225) in order to achieve a deep area of illumination (i.e., further from its exit opening 225). Ring-reflector illumination source 200A is configured to have the light from its LEDs 231 reflected at a less-shallow angle (e.g., by a face 2211B that is at an angle of approximately 47 degrees from the plane of its exit opening 225) in order to achieve a shallower area of illumination (i.e., closer to exit opening 225).

In one embodiment, ring reflector 220 is fabricated by turning on a lathe a blank of aluminum, stainless steel, plastic, glass or other suitable material to generate a circularly symmetric reflective face (e.g., conical-section face 2211) (i.e., the surface of the cross section shown is a straight line at an angle of 52 degrees from the plane of exit opening, i.e., 38 degrees from the optical axis 299), which is then polished and/or chrome plated to enhance its reflectivity at a wavelength of ring-light source 230. In another embodiment, ring reflector 221 is cast, e.g., by injection molding, from a suitable plastic, and then coated by well known methods with a reflective coating of chrome, gold or other metal, alloy, or multiple optical coating layers to enhance its reflectivity at one or more selected wavelengths of ring-light source 230. (These manufacturing methods can apply to any of the ring reflectors described below.)

Figure 2J:
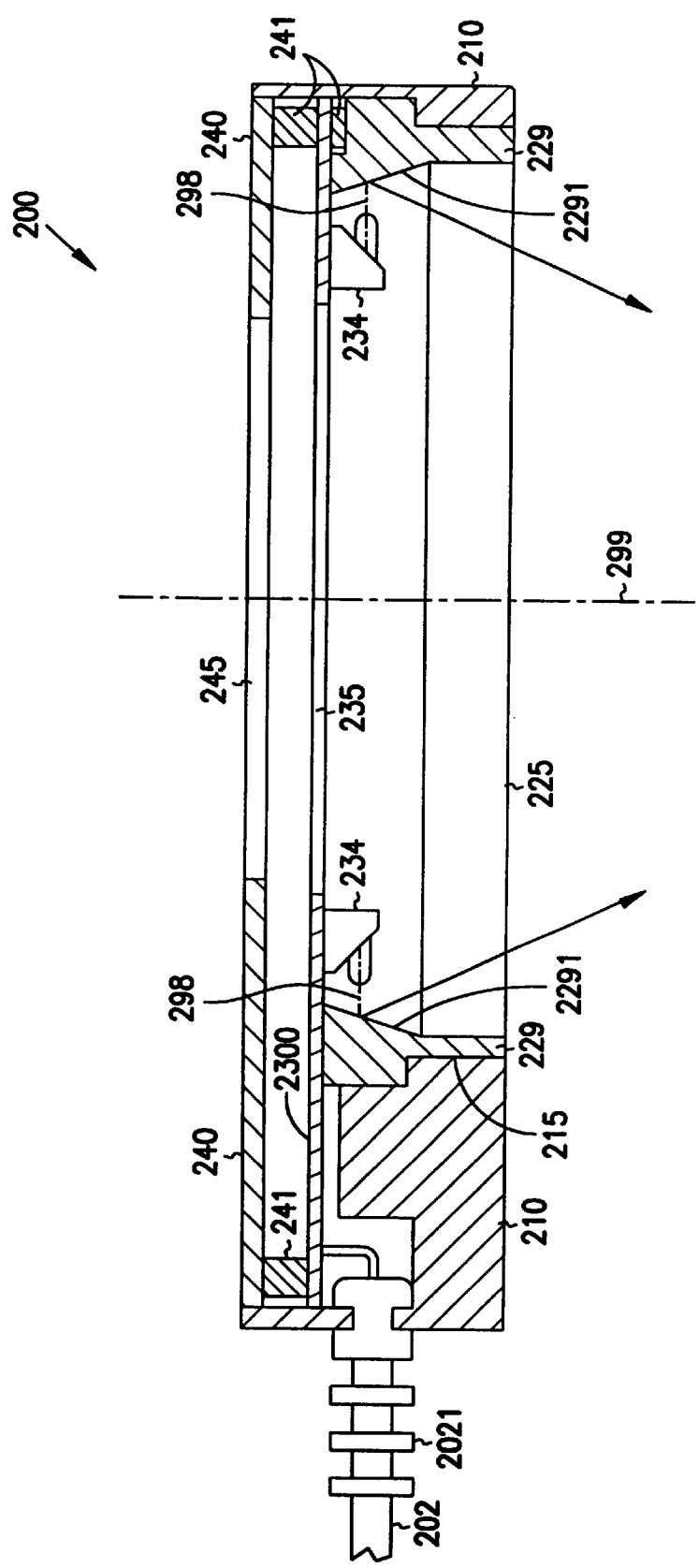
FIG. 2J is a cut-away side view of an alternative ring-reflector illumination source 200 according to one embodiment of the present invention.
Figure 4A:
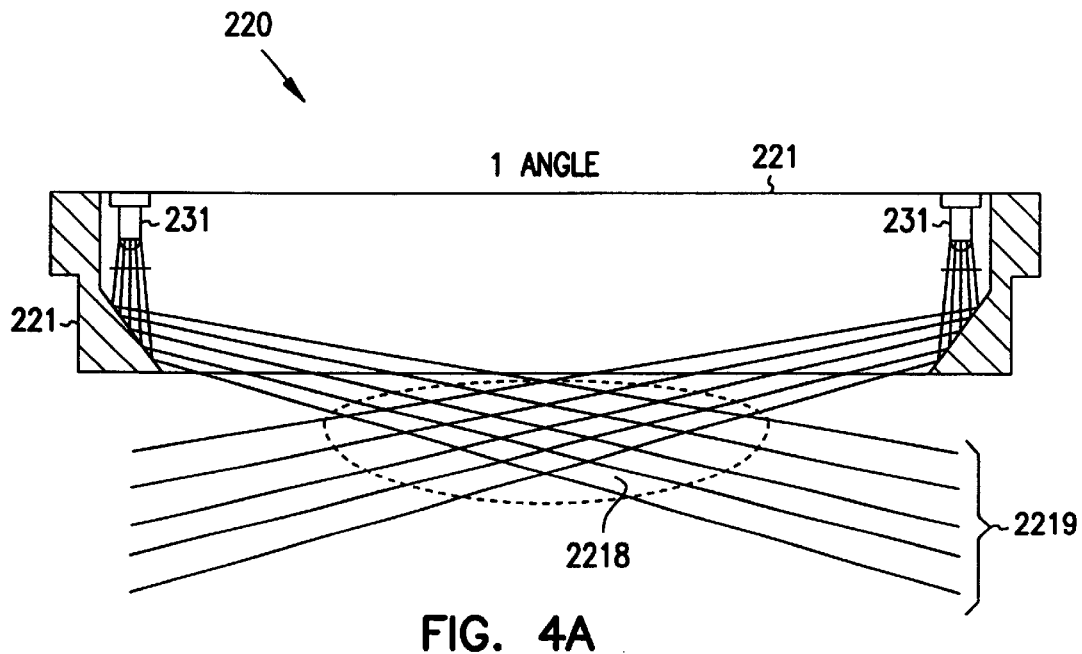
FIG. 4A is a cut-away side schematic of the ring reflector 220 of FIG. 3A showing the light pattern generated.

FIG. 2J is a cut-away side view of an alternative ring-reflector illumination source 200 according to one embodiment of the present invention. In this embodiment, each LED 234 is mounted on PCB 2300 in a circle around PCB opening 235 such that its light-emission focal centerline 298 is directed along a line radially perpendicular to optical axis 299 (i.e., the light is directed radially outward, centered on an emission plane that is perpendicular to optical axis 299). Ring reflector 229 is configured so that the emission plane intersects its operative reflective surface 2291, which redirects the light to a darkfield pattern (such as pattern 2218 as shown in FIG. 4A).

Darkfield illumination patterns, often used in microscopy applications, involve illumination in which light approaches the object (i.e., object 160) at an angle oblique or perpendicular to the optical axis, in order to minimize or eliminate light from the illumination source entering the camera (or microscope) lens either directly, or by reflection off some background object behind the object of interest. Thus, one application of the present invention is to provide darkfield illumination within, for example, a food container or beverage can 160, without illuminating the bottom of the can, e.g., in order to check for foreign objects within a clear beverage. One embodiment of darkfield illumination of the present invention is thus particularly useful for spotting foreign objects within open opaque aluminum cans, while minimizing light reflecting off the bottom of the can towards the camera. In one such embodiment, a pattern 2218 is designed so as to illuminate as deep as possible within a can 160 while minimizing illumination of the bottom of the can 160. The embodiments 221, 222, 223 of ring reflector 220 are particularly useful for generating such darkfield illumination patterns, since these ring reflectors 220 block the light from LEDs 231 that travels generally in the direction of the optical axis and that otherwise could illuminate background below the object of interest.

In contrast, other applications benefit from a deep illumination pattern which also illuminates the bottom of the can or food container. In one such embodiment, a pattern 2218 is designed so as to illuminate as deep as possible within a can 160 including illumination of the bottom of the can 160. The embodiments 229 (FIG. 2J) of ring reflector 220 is particularly useful for generating such darkfield illumination patterns, since these ring reflectors 220 block the light from LEDs 231 that otherwise could illuminate below the object of interest.

All of the embodiments shown are useful for inspecting electrical components, and in particular, components or substrates having ball-grid arrays of connector pads. Ball-grid arrays, such as IBM Corporation's C4 controlled-collapse connectors, generally include rectangular grids of spherical connector balls (i.e., tiny solder balls), that are used to simultaneously connect multiple signals from chips to modules, or modules to boards.

In the embodiment shown in FIG. 2J, the reflective surface 2291 is a single conical section; in other embodiments, this reflective surface is replaced by two conical sections (in a manner similar to that shown in FIG. 3B below); a circularly symmetric parabolic or other curved section (in a manner similar to that shown in FIG. 3C below); a series of facets (in a manner similar to that shown in FIG. 3E below), or a configurable reflective surface (in a manner similar to that shown in FIGS. 3F, 3G, or 3H below).

Figure 3A:
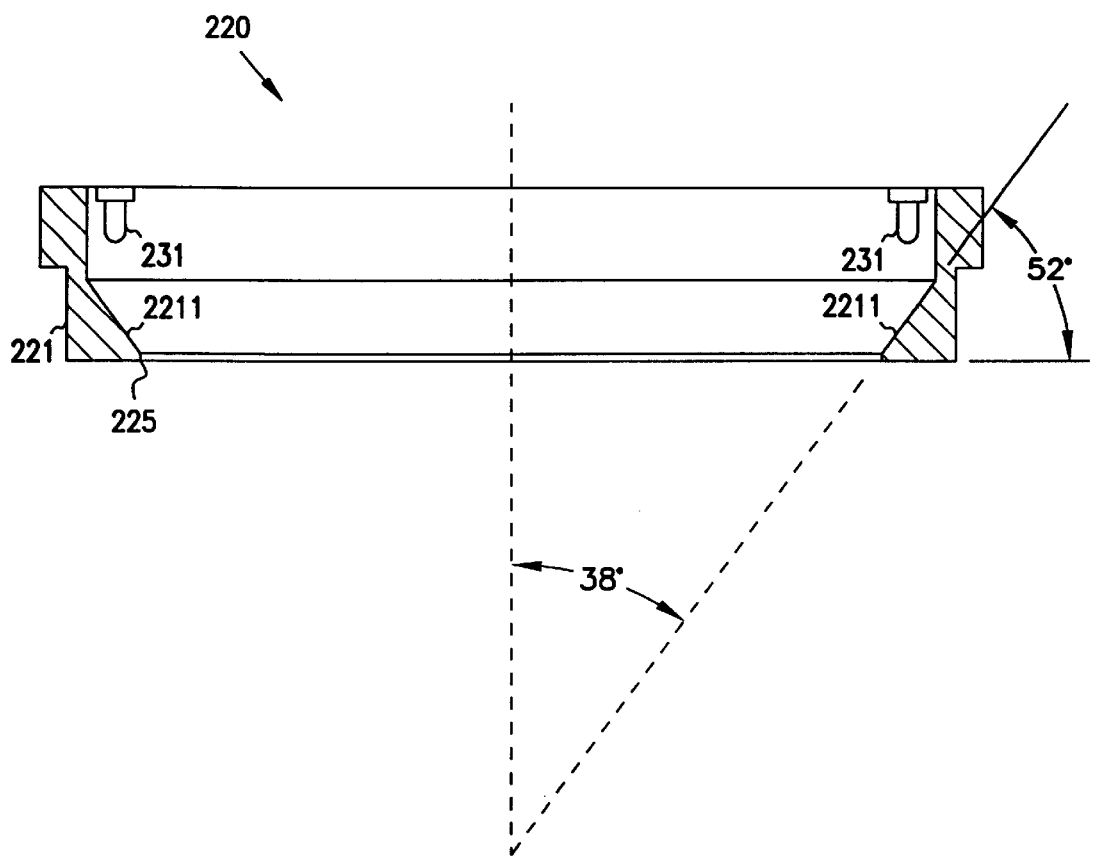
FIG. 3A is a cut-away side view of one ring reflector 220 according to one embodiment of the present invention.
Figure 5A:
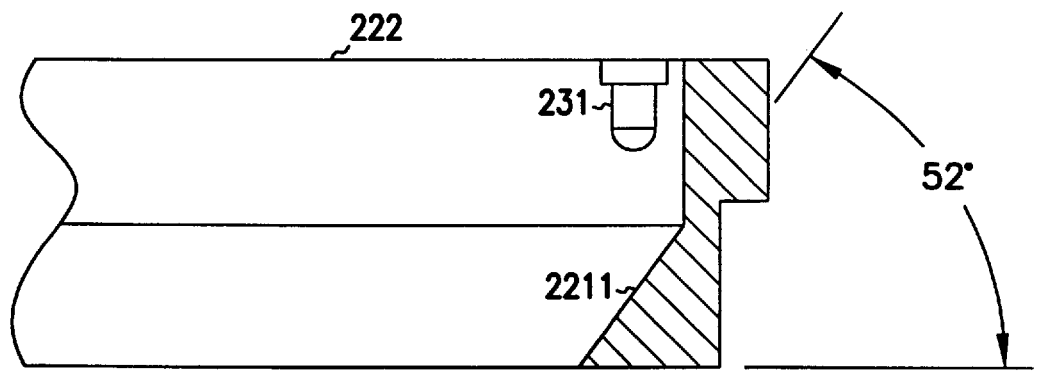
FIG. 5A is an enlarged cut-away side schematic of the ring reflector 220 of FIG. 3A.

FIG. 3A is a cut-away side view of one ring reflector 220 according to one embodiment of the present invention. In this embodiment, ring reflector 221 is a circularly symmetric conical-section reflective face 2211 (i.e., the surface of the cross section shown is a single straight line at an angle of approximately 52 degrees from the plane of exit opening, i.e., approximately 38 degrees from the optical axis 299). In this embodiment, the spread half-angle of light emission from the LEDs 231 is not significantly changed by reflecting off of surface 2211, and continues to diverge at approximately the same half-angle as before reflection (although now directed along a cone converging towards optical axis 299) thus providing a relatively broad spread of light below exit opening 225, as shown in FIG. 5A. Since the angle of incidence (approximately 38 degrees) is equal to the angle of reflection (also approximately 38 degrees), the cone of the centerlines of the LEDs approached the optical axis 299 at an angle of approximately 76 degrees. In other embodiments, the angle of face 2211 is set to other values to achieve the lighting pattern desired. In one embodiment, the lower edge of face 2211 is given a small chamfer (e.g., 0.02 inches) to reduced the danger to a user of otherwise sharp edges. In one embodiment, the length of face 2211, the distance from face 2211 to LEDs 231 (e.g., in one embodiment, this is made as close as possible), and the half-angle of light emission of the LEDs 231 (e.g., in one embodiment, LEDs are specified to have a small half-angle), are together configured such that most or all of the light emitted from LEDs 231 is reflected by face 2211 (rather than passing directly through exit opening 225). FIG. 5A is an enlarged cut-away side schematic of the ring reflector 220 of FIG. 3A.

In one such embodiment, particularly useful for darkfield microscopy, ring reflector 221 is a circularly symmetric conical-section reflective face 2211 having an angle of approximately 45 degrees from the plane of exit opening, i.e., approximately 45 degrees from the optical axis 299). In this embodiment, the spread half-angle of light emission from the LEDs 231 is not significantly changed by reflecting off of surface 2211, and continues to diverge at approximately the same half-angle as before reflection (although now directed along a cone diverging towards optical axis 299) thus providing a relatively broad spread of light within ring reflector 221 within exit opening 225. Since the angle of incidence (approximately 45 degrees) is equal to the angle of reflection (also approximately 45 degrees), the cone of the centerlines of the LEDs approached the optical axis 299 at an angle of approximately 90 degrees (perpendicular). For example, a glass slide could be placed flush against exit opening 225, with the specimen suspended in water above the slide and within such a ring reflector 221, whereby only light impinging on the specimen is visible through the lens of the camera or microscope.

In another such embodiment, the arrangement of FIG. 2B is inverted (i.e., with cover 240 further from the lens of camera 140 (or the microscope) and exit opening 225 closer to camera 140 (or the microscope)), such that the lens of the camera 140 (or microscope) is above, and on the same side of ring-reflector illumination source 200 as, exit opening 225. In this case, the glass slide is placed on top of exit opening 225 (towards the lens) with the specimen in a liquid above the slide, an opening 245 (now at the bottom) is covered with a non-reflective black surface such as black felt. In this way, the specimen is illuminated at oblique angles from below, with a darkfield illumination.

Figure 3B:
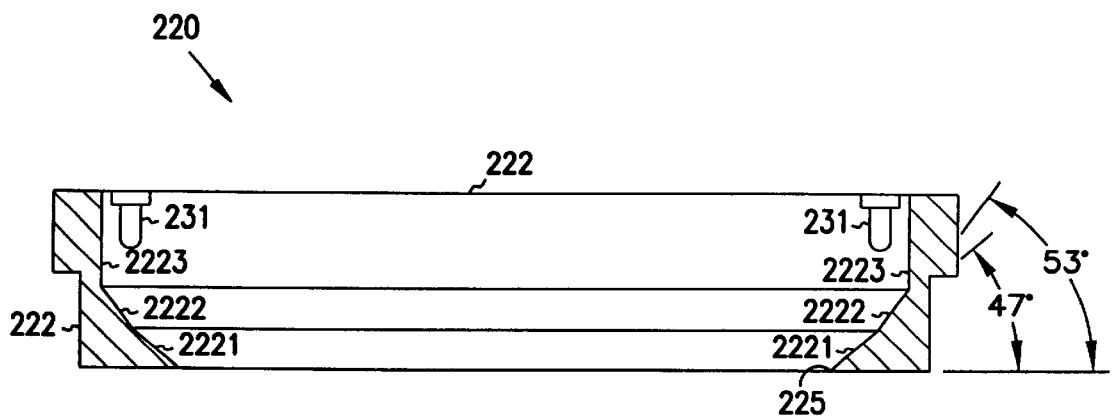
FIG. 3B is a cut-away side view of another ring reflector 220 according to one embodiment of the present invention.
Figure 5B:
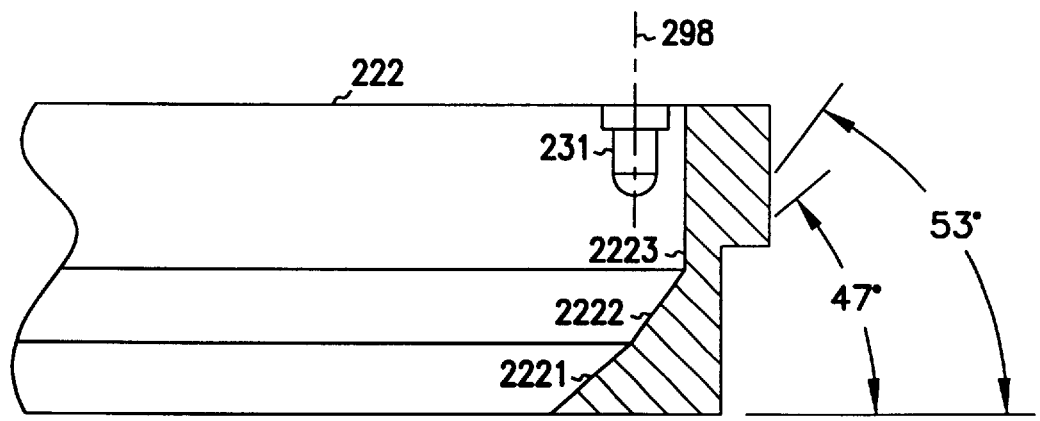
FIG. 5B is an enlarged cut-away side schematic of the ring reflector 220 of FIG. 3B.

FIG. 3B is a cut-away side view of another ring reflector 220 according to one embodiment of the present invention. In this embodiment, ring reflector 222 is a circularly symmetric reflective face having two adjacent conical-sections 2221 and 2222 (i.e., the surface of the cross section shown is two straight-line chords at angles of approximately 47 and 53 degrees respectively from the plane of exit opening, i.e., approximately 37 and 43 degrees from the optical axis 299, the chords meeting at a concave intersection). In this embodiment, the spread half-angle of light emission from the LEDs 231 is narrowed by reflecting off of surfaces 2221 and 2222, and continues to diverge at a smaller half-angle than before reflection (although now redirected along a cone converging towards optical axis 299) thus providing a relatively smaller spread of light below exit opening 225, as shown in FIG. 5B. Since the two conical-section surfaces 2221 and 2222 form a somewhat concave surface having an average angle of incidence and reflection of 40 degrees, the cone of the centerlines of the LEDs approached the optical axis 299 at an angle of approximately 80 degrees. In other embodiments, the angles of faces 2221 and 2222 are set to other values to achieve the lighting pattern desired. In one embodiment, the angles of faces 2221 and 2222 are approximately 53 and 47 degrees respectively from the plane of exit opening (i.e., the reverse of the above case), thus forming a convex reflecting cross-section, and thus increasing the half-angle of dispersion of the emitted light.

FIG. 5B is an enlarged cut-away side schematic of the ring reflector 220 of FIG. 3B.

Figure 3C:
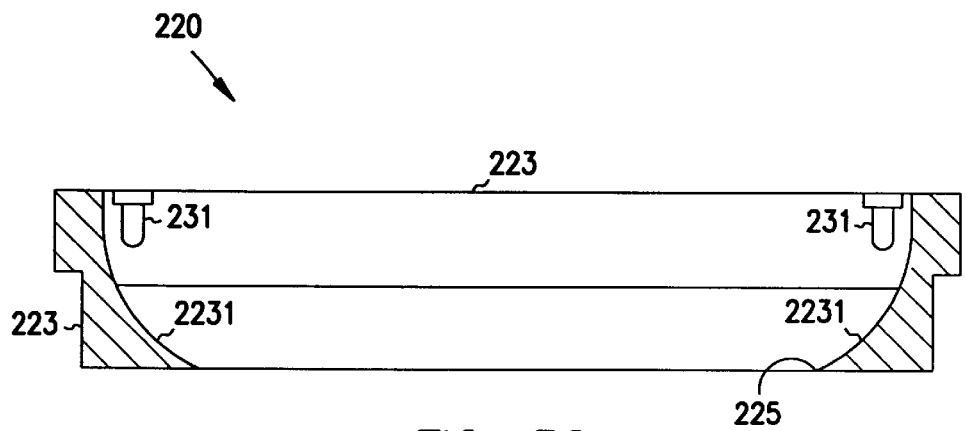
FIG. 3C is a cut-away side view of yet another ring reflector 220 according to one embodiment of the present invention.

FIG. 3C is a cut-away side view of yet another ring reflector 220 according to one embodiment of the present invention. In this embodiment, ring reflector 223 is a circularly symmetric reflective face having a cross section that is concave circular or concave parabolic 2231 (i.e., the surface of the cross section shown is a curved concave section of a circle or parabola at continuously varying angles from the plane of exit opening). In this embodiment, the spread half-angle of light emission from the LEDs 231 is narrowed by reflecting off of surface 2231, and continues to converge at a smaller half-angle than before reflection (although now redirected along a cone converging towards optical axis 299) thus providing a relatively smaller spread of light below exit opening 225, similar to as shown in Figure SB. By choosing an appropriate curved concave section, the focus provided by reflector ring 223 can be determined to the degree desired. By extension, by choosing an appropriate curved convex section, the additional divergence provided by reflector ring 223 can alternatively be determined to the degree desired.

Figure 3D:
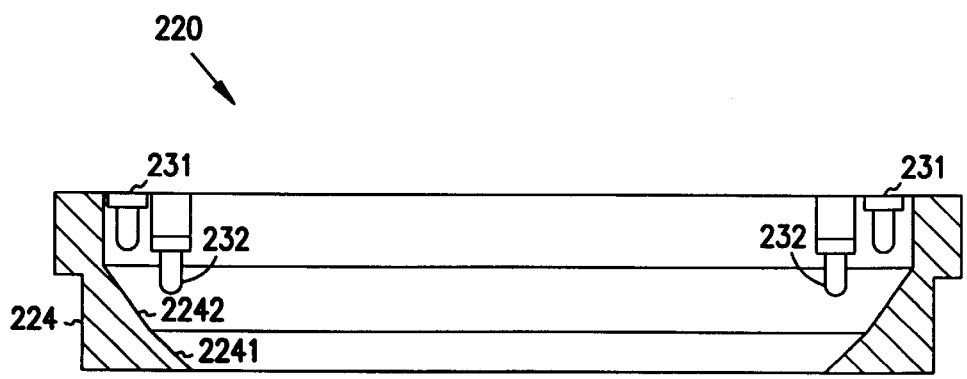
FIG. 3D is a cut-away side view of still another ring reflector 220 according to one embodiment of the present invention.

FIG. 3D is a cut-away side view of still another ring reflector 220 according to one embodiment of the present invention. In this embodiment, ring reflector 224 is a circularly symmetric reflective face having two adjacent conical-sections 2241 and 2242, and is otherwise identical to ring reflector 222 of FIG. 3B. Ring reflector 224 is configured to have the light from an outer row of LEDs 231 reflected by surface 2242, and to have the light from an inner row of LEDs 232 reflected by surface 2241. In one such embodiment, outer row of LEDs 231 emits light of a first color, and inner row of LEDs 232 of a second color, and are lit alternatively or simultaneously to achieve lighting effects as desired. In another such embodiment, outer row of LEDs 231 and inner row of LEDs 232 both emit light of the same color, and are lit alternatively or simultaneously to achieve lighting effects as desired (i.e., shallow lighting, deep lighting, or both.

Figure 3E:
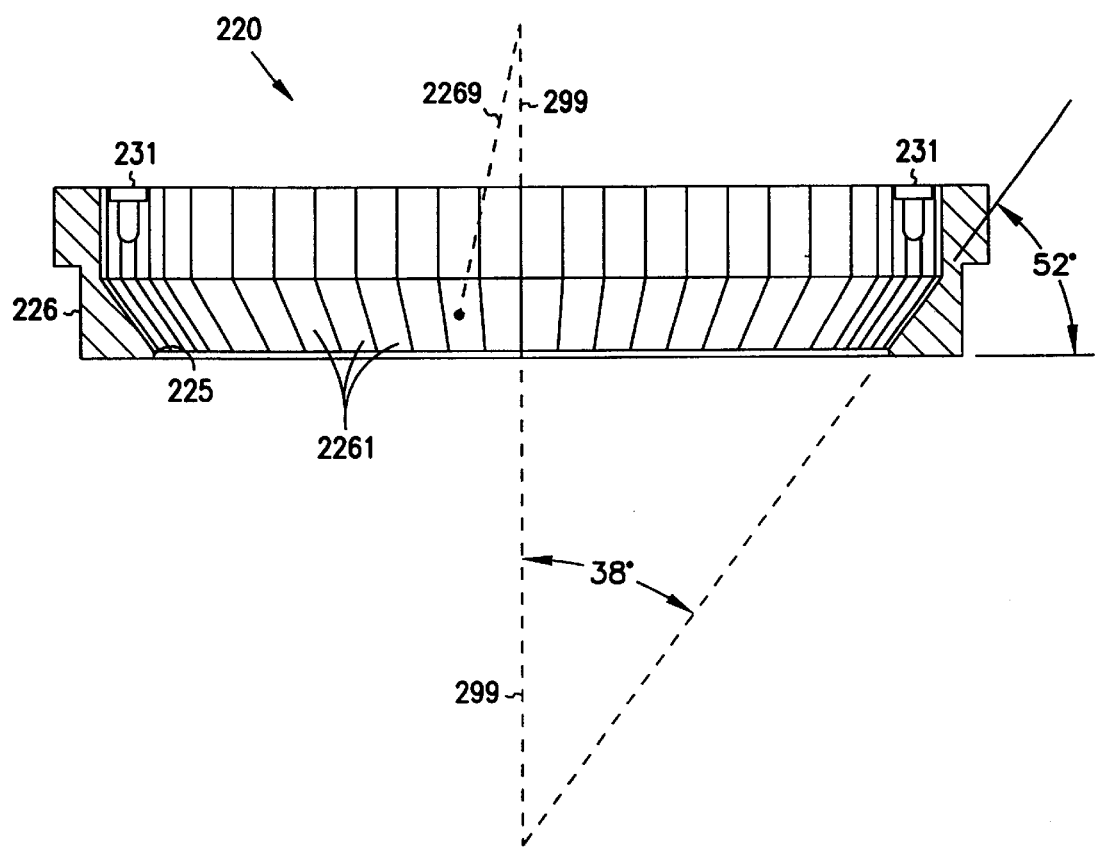
FIG. 3E is a cut-away side view of a facetted ring reflector 226 according to one embodiment of the present invention.

FIG. 3E is a cut-away side view of a facetted ring reflector 226 according to one embodiment of the present invention. In one such embodiment, for every facet 2261, a line 2269 drawn from the center of the facet perpendicular to the plane of the facet will intersect the optical axis 299 on order that the most amount of light will be centered on the optical axis. In another such embodiment, for every facet 2261, a line 2269 drawn from the center of the facet perpendicular to the plane of the facet will pass to the side of the optical axis 299 (e.g., approximately 1 or 2 centimeters (cm) to the side) in order that the light is spread onto a wider volume (still centered around the optical axis) than in the just-before described example. In a third such embodiment, for every facet 2261, a line 2269 drawn from the center of the facet perpendicular to the plane of the facet will pass through or pass to the side of the optical axis 299 by successively different amounts (e.g., a first facet perpendicular passes through the optical axis 299, the next adjacent facet perpendicular passes approximately 1 cm to the clockwise side, the next adjacent facet perpendicular passes approximately 2 cm to the clockwise side, and then the pattern repeats for each successive three facets) in order that the light is spread onto a wide volume, but now slightly more centered around the optical axis, than in the just-before described example.

Figure 3F:
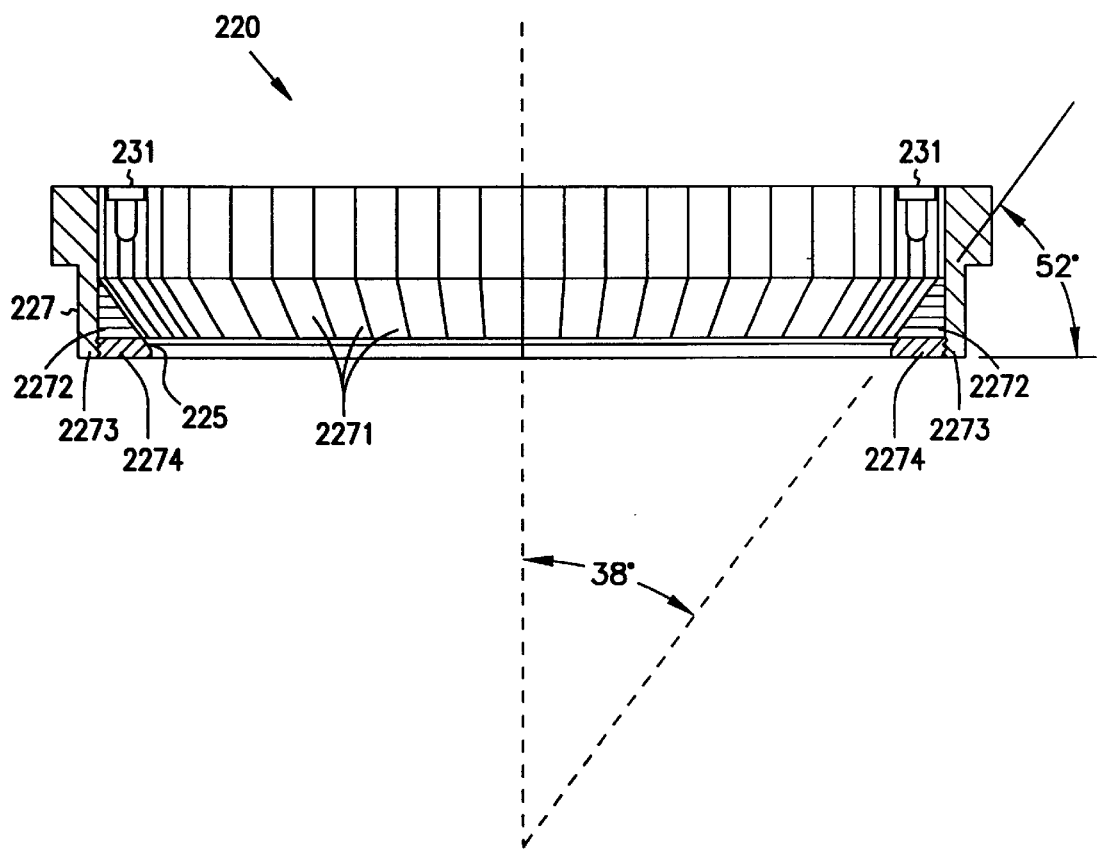
FIG. 3F is a cut-away side view of a configurable ring reflector 227 according to one embodiment of the present invention.
Figure 3G:
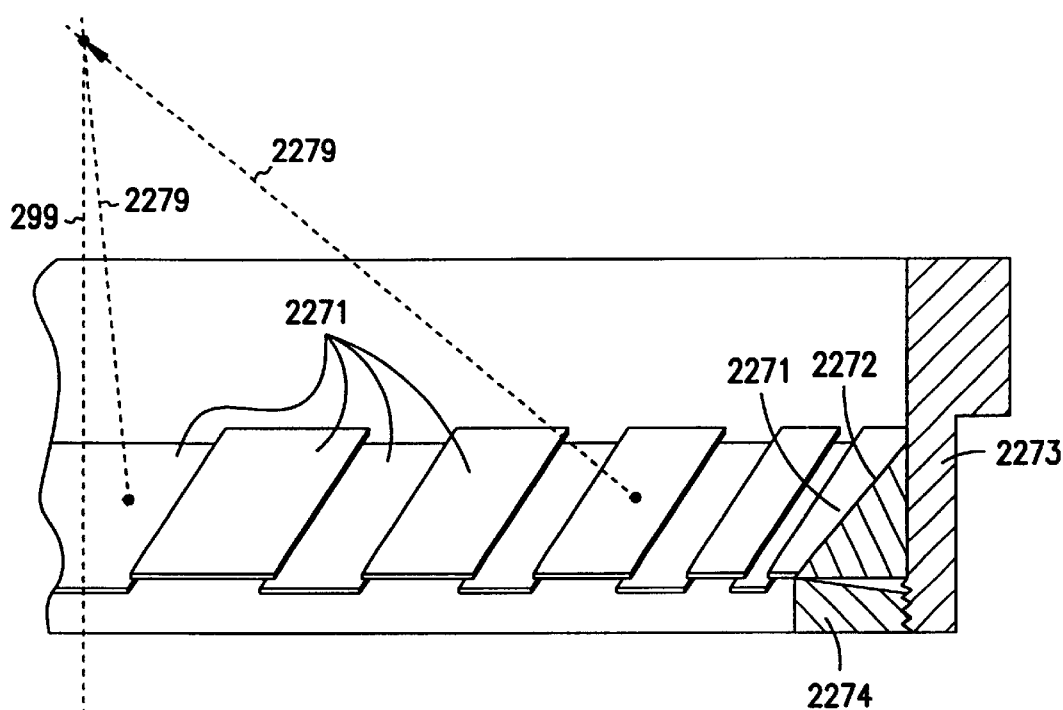
FIG. 3G is an enlarged cut-away side view of a configurable ring reflector 2273 having overlapped facets 2271 each pointing towards the optical axis 299.
Figure 3H:
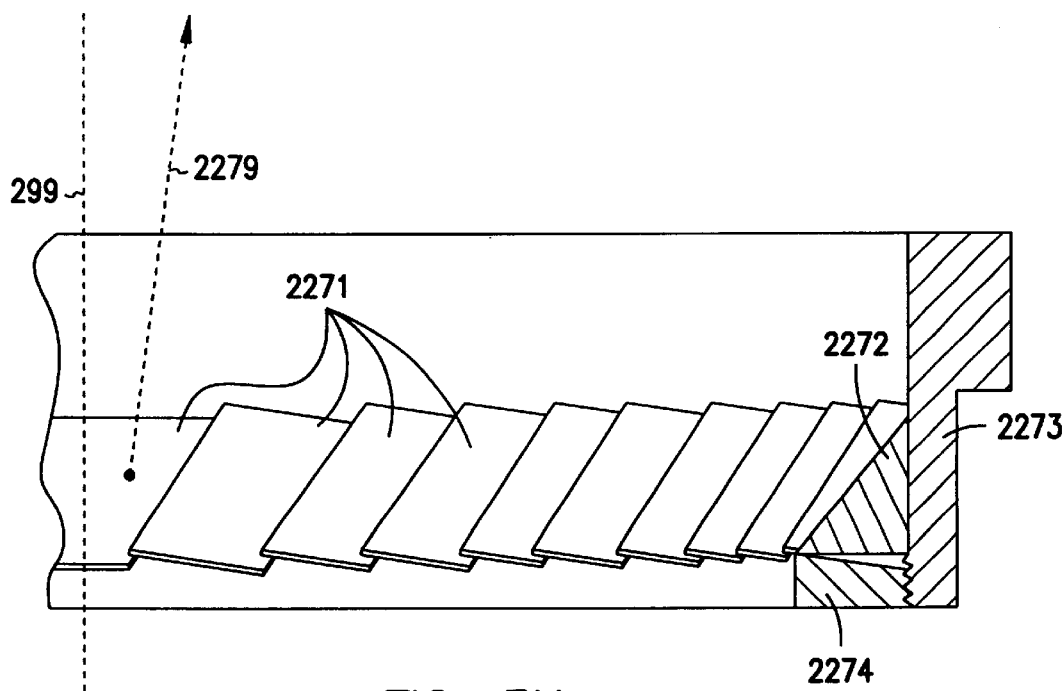
FIG. 3H is an enlarged cut-away side view of a configurable ring reflector 2283 having overlapped facets 2281 each pointing off to the side of the optical axis 299.

FIG. 3F is a cut-away side view of a configurable ring reflector 227 according to one embodiment of the present invention. In this embodiment, each facet 2271 is made of a thin reflective material such as a small trapezoid of aluminum, aluminized silicon, aluminized mylar, or other reflective chip, and is fastened to pliable focusing gasket 2272 preferably made of rubber or pliable plastic. Outside ring 2273, preferably made of metal such as aluminum, is permanently attached to pliable focusing gasket 2272 at their junction (e.g., by adhesive), and is threaded at the bottom of its inside circumference to accept threaded, tapered compression ring 2274. As compression ring 2274 is rotated into the threads of the inner bottom of outside ring 2272, it first contacts the inner diameter edge of pliable focusing gasket 2272, thus deflecting each facet 2271 upward at their bottom edges, while the top edges of each facet 2271 remains at the junction of pliable focusing gasket 2272 and outside ring 2273. This changes the angle of each facet 2271 (e.g., from a nominal undeflected angle of approximately 38 degrees to a larger angle). In one such embodiment, for every facet 2271, a line 2269 drawn from the center of the facet perpendicular to the plane of the facet will intersect the optical axis 299 on order that the most amount of light will be centered on the optical axis. In one such embodiment, every other facet has edges that overlay above the edges of each of its closest neighbors, as shown in FIG. 3G. In another such embodiment, every facet 2271 has its, e.g., left edge overlaying above the right edge of each of its closest left-hand neighbor, as shown in FIG. 3H, in order that, for every facet 2271, a line 2279 drawn from the center of the facet perpendicular to the plane of the facet will pass to the side of the optical axis 299 (e.g., approximately 1 or 2 centimeters (cm) to the right side in the example FIG. 3H) in order that the light is spread onto a wider volume (still centered around the optical axis) than in the just-before described example.

Figure 3I:
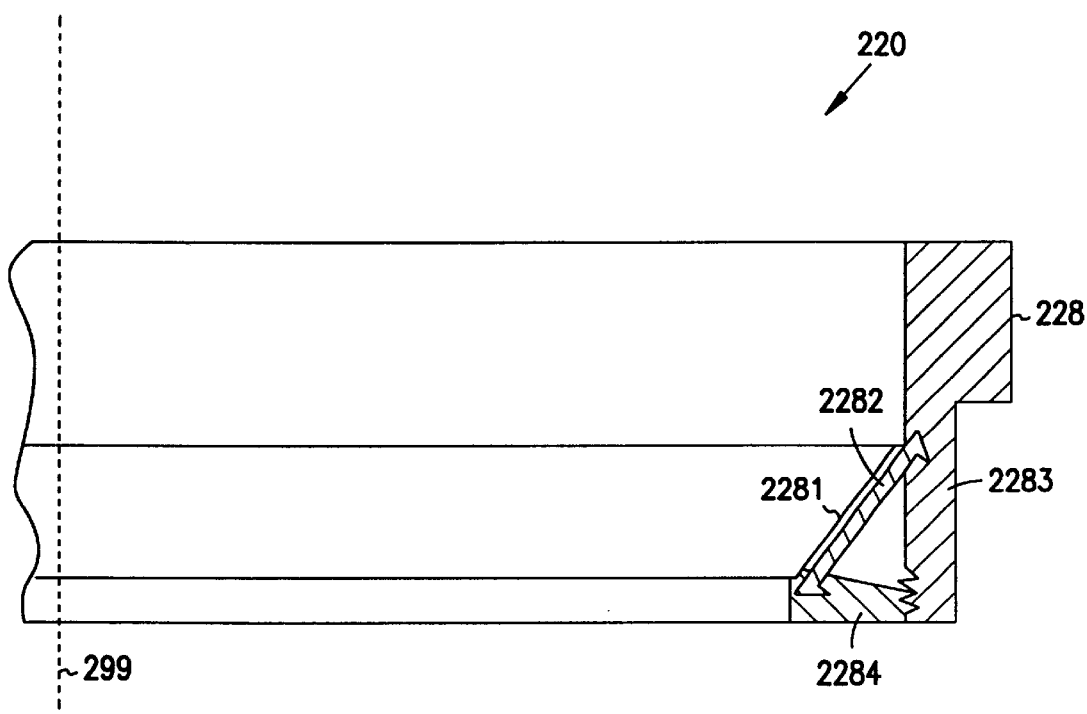
FIG. 3I is an enlarged cut-away side view of a configurable ring reflector 2283 having a stretchable reflective membrane 2281.

FIG. 3I is a cut-away side view of a configurable ring reflector 228 according to one embodiment of the present invention. In this embodiment, thin reflective surface 2281 is fastened to (or deposited on the surface of) stretchable focusing membrane 2282 preferably made of rubber or pliable plastic. Outside ring 2283, preferably made of metal such as aluminum, is permanently attached to stretchable focusing membrane 2282 at their junction (e.g., by adhesive or a dovetail joint), and is threaded at the bottom of its inside circumference to accept threaded, tapered stretching ring 2284. As stretching ring 2284 is rotated into the threads of the inner bottom of outside ring 2282, it releases some of the stretch of stretchable focusing membrane 2282, thus deflecting reflective surface 2281 upward at its bottom edge, while the top edge of reflective surface 2281 remains at the junction of stretchable focusing membrane 2282 and outside ring 2283. This changes the angle of reflective surface 2281 (e.g., from a nominal undeflected angle of approximately 38 degrees to a larger angle).

FIG. 4A is a cut-away side schematic of the single-conical-section ring reflector 221 of FIG. 3A showing the light pattern generated (having highest intensity within the dotted line volume 2218), which is sometimes called a darkfield-illumination pattern. In such a darkfield-illumination pattern, an object 160 located within A deeper pattern is generated by a shallower angle in reflector 221, and/or a wider half-angle of LEDs 231.

Figure 4B:
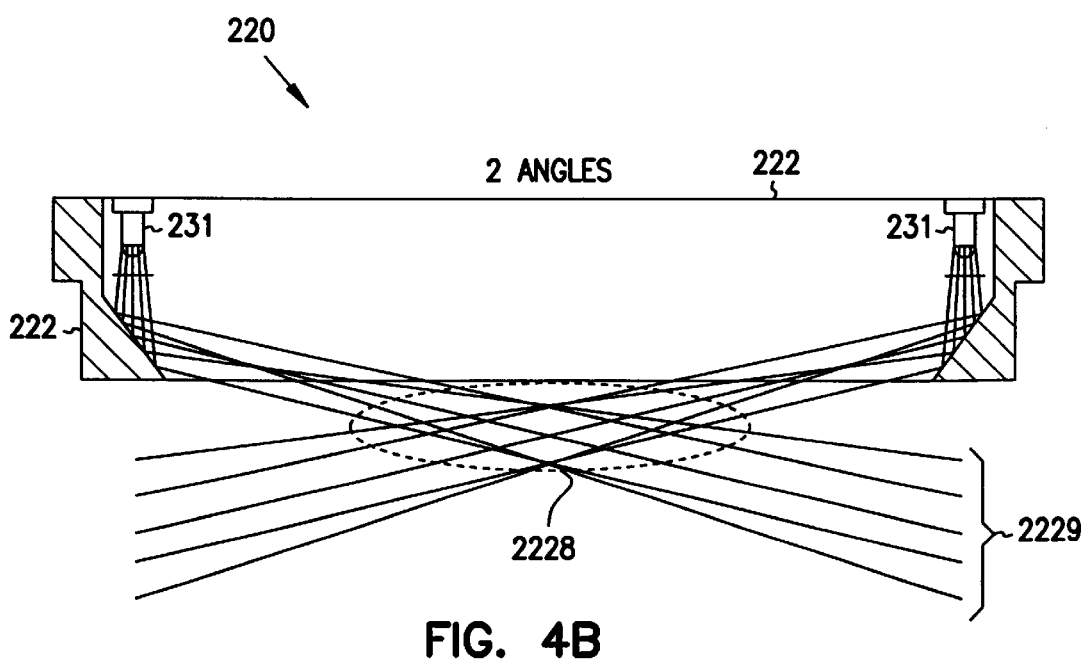
FIG. 4B is a cut-away-side schematic of the ring reflector 220 of FIG. 3B showing the light pattern generated.

FIG. 4B is a cut-away side schematic of the concave dual-conical-section ring reflector 222 of FIG. 3B showing the light pattern generated (having highest intensity within the dotted line volume 2228). A deeper pattern is generated by a shallower angles in reflector 222, and/or a wider half-angle of LEDs 231.

FIG. 5A is an enlarged cut-away side schematic of the ring reflector 220 of FIG. 3A.

FIG. 5B is an enlarged cut-away side schematic of the ring reflector 220 of FIG. 3B.

Figure 6:
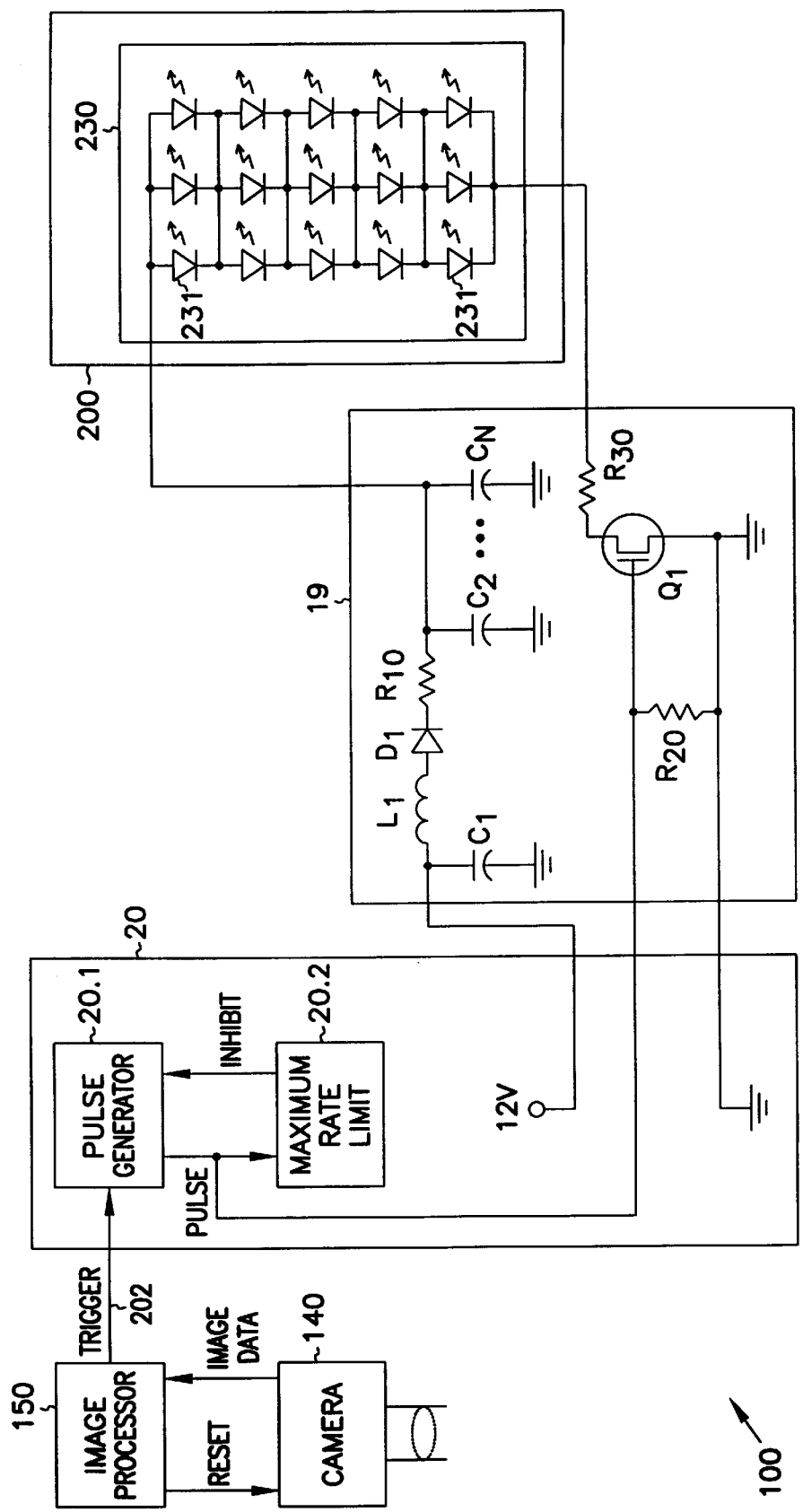
FIG. 6 is a schematic diagram of the LED drive electronics for one exemplary system 100.

FIG. 6 is a block diagram of the electrical connections for one embodiment of machine-vision illumination system 100. Image processor 150 sends a reset signal to camera 140, then shortly thereafter (or simultaneously) sends a trigger signal to power supply 20. Within power supply 20, the trigger signal activates pulse generator 20.1 to generate a control pulse of a predetermined length. The control pulse is used to turn on transistor Q1 to generate a flash on LEDs 231, which is current-limited (if desired) by resistor R30. The control pulse also activates the maximum-rate-limit circuit 20.2, which inhibits any further control pulses from pulse generator 20.1 for a predetermined amount of time.

The 12-volt signal from power supply 20 is filtered by the low-pass filter comprising C1, L1, D1, and R10, and charges capacitors C2 through $C_N$ (in one embodiment, N is 12). In one such embodiment, C1 through C12 are each 2200 $\mu$F, L1 is 40 $\mu$H iron-core, D1 as a 1N4001 diode, and R10 is a 0 ohm conductor (i.e., a short). C2 through $C_N$ are discharged through, e.g., fifteen LEDs 231 as shown in the circuit diagram, which in this embodiment are wired in a parallel-series manner as shown, (in another embodiment, sixty LEDs arranged in a single row are used; in another embodiment, 150 LEDs are used, each in a similar serial-parallel-wired connection circuit), and R30 and Q1, as activated by the above-described control pulse. In one such embodiment, R30 is replaced by a zero-ohm conductor, and the voltage drop across the LEDs 231 and Q1 is used to self-limit the current through the LEDs 231. The control pulse is fed across resistor R20, which in one embodiment is 100KΩ, to develop the necessary voltage for driving transistor Q1, which in this embodiment is a MTP75N05HD MOSFET.

Figure 7:
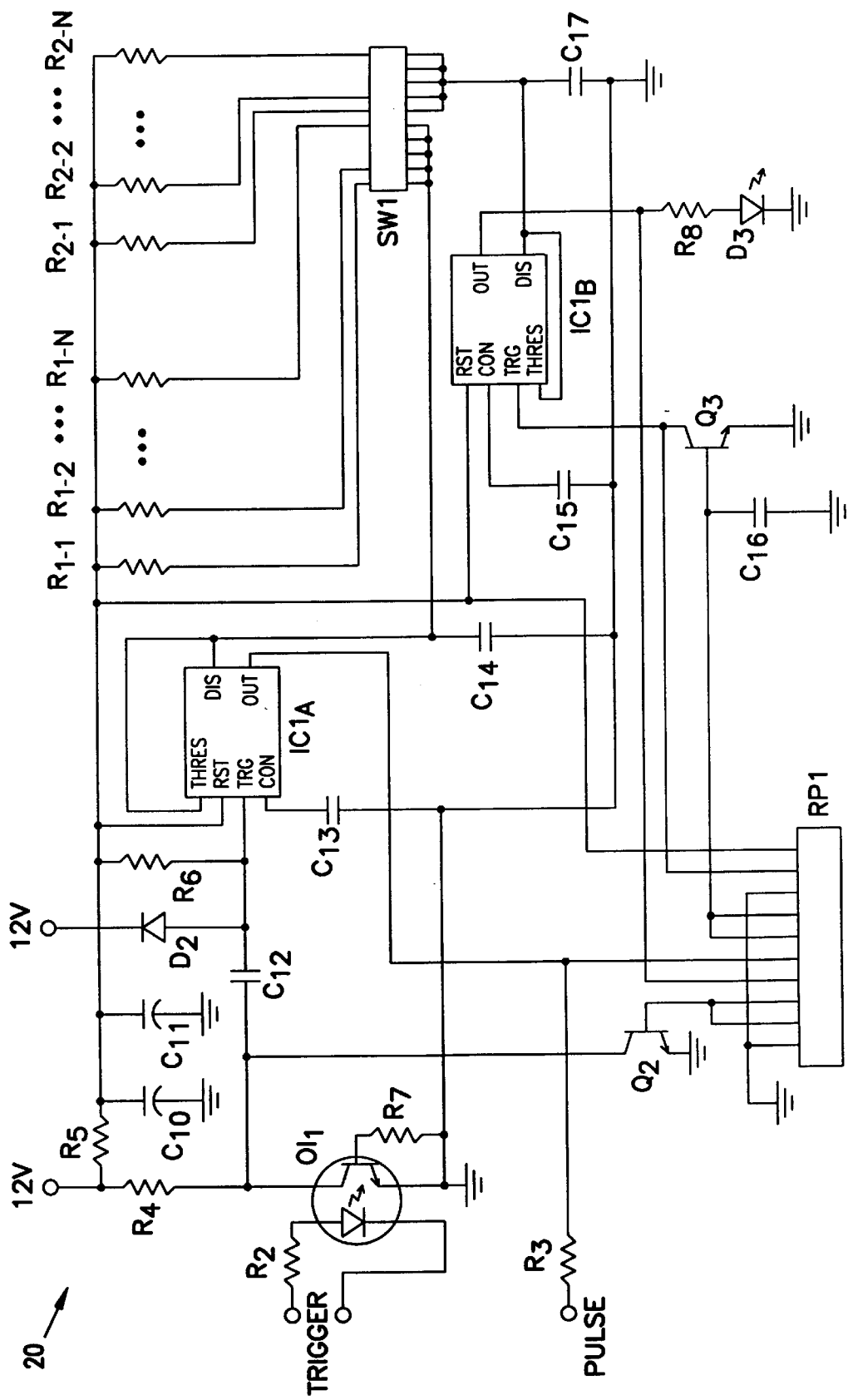
FIG. 7 is a schematic diagram of one exemplary power supply 20.

FIG. 7 is a more-detailed schematic diagram of power supply 20. The input trigger is fed through resistor R21 to drive the input of opto-isolator OI1. The output of opto-isolator OI1 is coupled through capacitor C12 (and the associated circuit R4, R6 and D2) to the TRG input of timer circuit $1C1_A$. (IN one embodiment, timers $1C1_A$ and $1C1_B$ are each ½ of a 556-type dual timer.) The timing constant of timer $1C1_A$ is set by C14 and R1-x, (where x is selected from 1 through N), and determines the pulse width of the control pulse driving Q1, and thus the LEDs 231. In one embodiment, five selectable pulse widths are predetermined and selected by SW1, which is a five-way exclusive dual-pole-single-throw switch, wherein one resistor of the set R1-1 through R1-N is selected for connection to the DIS input pin of 1C1A, and a corresponding one resistor of the set R2-1 through R2-N is selected for connection to the DIS input pin of $1C1_B$. The timing constant of timer $1C1_B$ is set by C17 and R2-x, (where x is selected from 1 through N), and determines the minimum time between control pulses driving Q1, and thus the LEDs 231. In one embodiment, the five selectable predetermined pulse widths are 25 microseconds ($\mu$s), 50 $\mu$s, 100 $\mu$s, 200 $\mu\mu$s and 500 $\mu$s; the corresponding maximum pulse rates controlled by maximum rate limit circuit 20.2 are 200 Hz, 120 Hz, 60 Hz, 30 Hz, and 10 Hz, respectively, and are predetermined and selected by SW1. Thus, in the embodiment which uses a 60 Hz camera image rate, 100 $\mu$s-long control pulses are used to activate LEDs 231. In one embodiment, it is desired to have an average LED illumination intensity of at least ten times the ambient light; thus, when camera 140 is taking one frame every 16.7 milliseconds, a 100 microsecond pulse should be at least 1670 times as intense as the ambient light. In one such an embodiment, a shroud is used to reduce the ambient light, and a red filter (substantially transparent to the peak wavelength of ring-reflector illumination source 200) is placed over the lens of camera 140 in order to reduce ambient light and pass the light of ring-reflector illumination source 200. The control pulse output signal is driven through resistor R31.

In one embodiment, opto-isolator OI1 is a 4N37-type part, resistor R2 is 100 Ω, resistor R3 is 1000 Ω, resistor R7 is 1 MΩ, resistor R8 is 1KΩ and visible-color LED D3 indicates when the circuit is active, resistor R4 is 4700 Ω, resistor R5 is 10 Ω, resistor R6 is 10KΩ, diode D2 is a 1N914, resistor R1-1 is 2.26KΩ, resistor R1-2 is 4.53KΩ, resistor R1-3 is 9.0KΩ, resistor R1-4 is 18.2KΩ, resistor R1-5 is 45.3KΩ, resistor R2-1 is 37.4KΩ, resistor R2-2 is 75KΩ, resistor R2-3 is 150KΩ, resistor R2-4 is 301KΩ, resistor R2-5 is 909KΩ, C14 is 0.01 µF, C17 is 0.1 µF, C12 is 0.001 µF, C10 is 100 µF, C11 is 0.1 µF, C13, C15, and C16 are each 0.01 µF, Q2 and Q3 are each 2N3904 NPN transistors, and RP1 is a 10KΩ resistor pack.

"Chromatic aberration" is where a lens focuses different wavelengths of light at different focal points. "Spherical aberration" occurs when light from the edges of a circularly-curved lens are focused at different distances that light through the center of the lens. Circularly curved lenses are used since they are cheaper to produce a lens with a spherical curved surface than one in which the curvature changes. The problem, however, is that spherical aberration can occur, where the edges of the lens focus the light waves at a different point from the center of the lens, causing lack of sharpness. Regarding the oblique rays passing through the lens, these fall on different parts of the "image plane," in a blur rather than being superimposed. This slightly different aspect of spherical aberration is called coma. To overcome this can be costly, but mirror-type ring-reflector focusing elements 220 do not suffer from these aberrations.

The process of the present invention is unlike conventional illumination sources since it is compact, generates a light source from more than one point source with suitable brightness in order to reduce shadows, focuses the light source into a broad, deep, multidirectional source illuminating a volume with light rays that approach generally the optical axis of the machine-vision system at oblique angles from a ring that surrounds the optical axis, so that even extremely small parts can be adequately inspected and accurately viewed or measured with machine-vision system 100. Another aspect of the present invention is to provide a compact illumination source, preferably monochromatic, which can be focused to provide uniform multi-directional light onto all surfaces that are viewable by the machine vision camera. Yet another aspect of the present invention is to have such an LED illumination source be pulsed with a relatively high-power, low duty-cycle power source.

In one embodiment, most or all interior surfaces of ring-reflector illumination source 200 except the operative reflecting surface (e.g., surfaces 2211, 2221, 2222, or 2231) have an anti-reflective (e.g., flat black) surface to prevent stray reflections. In one embodiment, the flat black surface is obtained by applying flat black paint. In another embodiment, the flat black surface is obtained through use of a standard black anodization process.

It is to be understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. An illumination system for illuminating an object for machine-vision, the system having an optical axis, comprising:
    a ring light source that comprises:
    a substantially ring-shaped flashtube emitting light from a light-emitting region disposed substantially in a plane that intersects the optical-axis, the light-emitting region disposed at least a first distance from the optical axis and less than a second distance from the optical axis; and
    a first ring reflector, the ring reflector having an exit opening though which the optical axis passes, the emitted light from the ring light source being generally directed centered on lines that intersect a reflecting surface of the ring reflector, the ring reflector reflecting the emitted light from the light source though the exit opening inwards and generally towards the optical axis; and
    an enclosure generally surrounding the flashtube but having a elongated aperture disposed between the ring-shaped flashtube and the ring reflector, wherein the elongated aperture allows light from the flashtube to fall on a reflecting surface of the ring reflector.

2. The illumination system as recited in claim 1, further comprising a focusing element, disposed in a path of the emitted light from the ring light source, and that includes a cylindrical ring lens having at least one convex face.

3. The illumination system as recited in claim 1, wherein the ring reflector has a surface that enhances its reflectivity at one or more selected wavelengths of the ring light source.

4. The illumination system as recited in claim 3, wherein the first ring reflector and ring light source are configured to produce a darkfield illumination.

5. The illumination system as recited in claim 1, wherein the first ring reflector includes a reflective surface that comprises a first conical section.

6. The illumination system as recited in claim 5, wherein the first conical section includes a reflective surface at a first conical angle to the optical axis.

7. The illumination system as recited in claim 1, wherein the first ring reflector includes a reflective surface that comprises a plurality of adjoining conical sections.

8. The illumination system as recited in claim 7, wherein the plurality of adjoining conical sections includes a first conical section having a reflective surface at a first conical angle to the optical axis, and a second conical section having reflective surface at a second conical angle to the optical axis, the second conical angle being different than the first conical angle.

9. The illumination system as recited in claim 1, wherein the first ring reflector includes a reflective surface that comprises a circularly-rotated parabolic section.

10. The illumination system as recited in claim 1, wherein the first ring reflector includes a reflective surface that is configurable to change at least one angle at which the reflective surface reflects light.

11. The illumination system as recited in claim 1, wherein the first ring reflector includes a reflective surface that comprises a plurality of reflective facets.

12. The illumination system as recited in claim 11, wherein, for a plurality of the facets, a line normal to a facet surface passes through the optical axis.

13. A method for illuminating an object located along an optical axis, comprising the steps
    (a) emitting light from a light source that includes a ring-shaped flashtube disposed substantially along a circle disposed perpendicular to and centered on the optical axis, the light-emitting portion of the flashtube disposed at least a first distance from the optical axis and less than a second distance from the optical axis; and
    (b) reflecting the emitted light from the light source inwards and generally towards the object at the optical axis or in an area around the optical axis, wherein the object is an electrical connector, and further comprising the step of acquiring a machine-vision image of the electrical connector.

14. A method for illuminating an object located along an optical axis, comprising the steps (a) emitting light from a light source that includes a ring-shaped flashtube disposed substantially along a circle disposed perpendicular to and centered on the optical axis, the light-emitting portion of the flashtube disposed at least a first distance from the optical axis and less than a second distance from the optical axis; and (b) reflecting the emitted light from the light source inwards and generally towards the object at the optical axis or in an area around the optical axis, further comprising the step of focusing the emitted light to a circular line.

15. A method for illuminating an object located along an optical axis, comprising the steps of:

(a) emitting light from a light source that includes a ring-shaped flashtube disposed substantially along a circle disposed perpendicular to and centered on the optical axis, the light-emitting portion of the flashtube disposed at least a first distance from the optical axis and less than a second distance from the optical axis;

(b) focussing the emitted light through a circular cylindrical ring lens; and (c) reflecting the emitted light from the light source inwards and generally towards the object at the optical axis or in an area around the optical axis.

16. A machine-vision illumination system, comprising:

an imaging device disposed along an optical axis to receive an image of an object;

an image processor coupled to the imaging device that processes the image and produces machine-vision information; and a ring-light source to illuminate the object, wherein the ring light source comprises:

a ring-shaped flashtube disposed substantially along a circle disposed perpendicular to and centered on the optical axis;

a ring reflector configures to reflect light along at least one conical angle; and an enclosure having a slit disposed between the ring-shaped flashtube and the ring reflector, wherein the slit allows light from the flashtube to fall on a reflecting surface of the ring reflector.

17. The illumination system as recited in claim 16, further comprising a focusing element that includes a cylindrical ring lens having at least one convex face.

18. The machine-vision illumination system as recited in claim 16, wherein the ring reflector has a surface that enhances its reflectivity at one or more selected wavelengths of the ring light source.

19. The machine-vision illumination system as recited in claim 16, wherein the ring reflector and ring light source are configured to produce a darkfield illumination.

20. A method for illuminating an object located along an optical axis, comprising the steps (a) emitting light from a light source that includes a ring-shaped flashtube disposed substantially along a circle disposed perpendicular to and centered on the optical axis, the light-emitting portion of the flashtube disposed at least a first distance from the optical axis and less than a second distance from the optical axis; and (b) reflecting the emitted light from the light source inwards and generally towards the object at the optical axis or in an area around the optical axis, wherein the step of emitting light further comprises passing the emitted light through a circular slit.

21. The method for illuminating an object as recited in claim 15, wherein the step of reflecting light further comprises reflecting light at a plurality of discrete conical angles each defined by a conical section reflecting surface having a straight line cross section.

22. The method for illuminating an object as recited in claim 21, wherein the plurality of conical angles include a first conical angle to the optical axis, and a second conical angle to the optical axis, the second conical angle being different than the first conical angle.

* * * * *

UNITED STATES PATENT AND TRADEMARK OFFICE
CERTIFICATE OF CORRECTION

PATENT NO. : 6,238,060 B1
DATED : May 29, 2001
INVENTOR(S) : Bourn et al.

Page 1 of 1

It is certified that error appears in the above-identified patent and that said Letters Patent is hereby corrected as shown below:

Column 5,
Line 7, delete "FIG. 21" and insert -- FIG. 2I --, therefor.

Column 18, claim 13,
Line 52, delete "steps" and insert -- steps of: --, therefor.

Column 18, claim 14,
Line 67, delete "steps" and insert -- steps of: --, therefor.

Column 20, claim 20,
Line 16, delete "steps" and insert -- steps of: --, therefor.

Signed and Sealed this

Eleventh Day of December, 2001

Attest:

NICHOLAS P. GODICI
*Attesting Officer*  *Acting Director of the United States Patent and Trademark Office*